US009805146B2

(12) United States Patent
Lipowitz

(10) Patent No.: US 9,805,146 B2
(45) Date of Patent: Oct. 31, 2017

(54) ELECTRONIC EMULATION OF MATERIAL IMPEDANCE FOR STANDARDIZATION AND CALIBRATION OF ELECTROMAGNETIC MEASURING DEVICE

(71) Applicant: TransTech Systems, Inc., Schenectady, NY (US)

(72) Inventor: Frank H. Lipowitz, Rexford, NY (US)

(73) Assignee: TransTech Systems, Inc., Latham, NY (US)

( * ) Notice: Subject to any disclaimer, the term of this patent is extended or adjusted under 35 U.S.C. 154(b) by 771 days.

(21) Appl. No.: 14/206,514

(22) Filed: Mar. 12, 2014

(65) Prior Publication Data

US 2014/0278300 A1  Sep. 18, 2014

Related U.S. Application Data

(60) Provisional application No. 61/784,363, filed on Mar. 14, 2013.

(51) Int. Cl.
```
G06F 17/50      (2006.01)
G01N 27/22      (2006.01)
G01N 27/02      (2006.01)
```

(52) U.S. Cl.
CPC ....... *G06F 17/5009* (2013.01); *G01N 27/223* (2013.01); *G01N 27/026* (2013.01)

(58) Field of Classification Search
CPC . G06F 17/5009; G01N 27/223; G01N 27/026
USPC .......................................................... 714/28
See application file for complete search history.

(56) References Cited

U.S. PATENT DOCUMENTS

| 3,975,939 | A | * | 8/1976 | McLean | G01N 29/30 |
| | | | | | 73/1.86 |
| 5,511,425 | A | * | 4/1996 | Kleinert | G01N 29/069 |
| | | | | | 73/609 |
| 6,646,463 | B1 | * | 11/2003 | Hariton | H03H 11/485 |
| | | | | | 326/21 |
| 7,424,416 | B1 | * | 9/2008 | Cavanagh | G06F 17/5027 |
| | | | | | 703/13 |
| 2002/0032531 | A1 | * | 3/2002 | Mansky | B01J 19/0046 |
| | | | | | 702/21 |

(Continued)

*Primary Examiner* — Dwin M Craig
*Assistant Examiner* — Steven Crabb
(74) *Attorney, Agent, or Firm* — Hoffman Warnick LLC

(57) ABSTRACT

Apparatuses, systems, methods, and computer program products are presented for electronically emulating the impedance characteristics of materials, e.g., for standardizing and calibrating electromagnetic measuring devices for the measurement of physical properties of materials. The electronic impedance emulation apparatus according to some embodiments includes an electronic material emulation circuit in communication with the electromagnetic measuring device. The electronic material emulation circuit and the electromagnetic measuring device are controlled by a at least one computing device, which can control the frequency of signal(s) generated by the electromagnetic measuring device. The at least one computing device can instruct the electronic emulator to produce signals having complex impedance characteristics of the material under test at the test frequency. The emulation data can be stored and used for the calibration and/or standardization of the electromagnetic measuring device.

38 Claims, 19 Drawing Sheets

(56) References Cited

U.S. PATENT DOCUMENTS

| | | | | |
|---|---|---|---|---|
| 2006/0173670 A1* | 8/2006 | Engel | ............ | G06F 11/261 |
| | | | | 703/26 |
| 2006/0226857 A1* | 10/2006 | Troxler | ............ | G01N 27/223 |
| | | | | 324/663 |
| 2007/0176705 A1* | 8/2007 | Sutardja | ............ | H01L 23/34 |
| | | | | 331/176 |
| 2011/0260736 A1* | 10/2011 | Troxler | ............ | G01R 35/007 |
| | | | | 324/601 |
| 2013/0307564 A1* | 11/2013 | Colosimo | ............ | G01R 27/06 |
| | | | | 324/647 |
| 2014/0117970 A1* | 5/2014 | Kitagaki | ............ | H02J 1/10 |
| | | | | 323/318 |
| 2015/0137831 A1* | 5/2015 | Pluta | ............ | G01N 27/026 |
| | | | | 324/647 |
| 2016/0054247 A1* | 2/2016 | Colosimo | ............ | G01N 33/383 |
| | | | | 324/629 |
| 2016/0161624 A1* | 6/2016 | Pluta | ............ | G01V 3/12 |
| | | | | 324/327 |
| 2016/0197559 A1* | 7/2016 | Tan | ............ | H02P 9/007 |
| | | | | 363/35 |

* cited by examiner

ELECTRONIC EMULATION OF MATERIAL IMPEDANCE FOR STANDARDIZATION AND CALIBRATION OF ELECTROMAGNETIC MEASURING DEVICE

CROSS-REFERENCE TO RELATED APPLICATION

This utility application claims the benefit of U.S. Provisional Patent Application Ser. No. 61/784,363, filed on Mar. 14, 2013, which is hereby incorporated by reference in its entirety.

TECHNICAL FIELD

The presently disclosed subject matter relates to measurement devices. More particularly, the subject matter disclosed herein relates to the standardization and calibration of electromagnetic measuring devices.

BACKGROUND

Conventional calibration and standardization approaches for measurement devices have numerous shortcomings, such as: (1) extensive size and weight of the calibration material; (2) variability in the manufacture of materials currently used, causing the electrical characteristics to vary from sample to sample; and (3) the inability to match the electromagnetic response of calibration materials with intended materials under test over the range of frequencies used by the measuring devices. These conventional approaches result in inaccurate calibration of measurement devices, which makes use of those devices ineffective.

SUMMARY

The apparatuses, systems, methods and programs of the present subject matter relate to the calibration and standardization of electromagnetic density and moisture measuring devices. The present subject matter provides for electronically emulating the impedance characteristics of materials for standardizing and calibrating electromagnetic measuring devices for the measurement of physical properties of materials. The electronic emulator apparatus can include an electronic material emulation circuit in communication with the electromagnetic measuring device. The electronic material emulation circuit and the electromagnetic measuring device may be controlled by a computer means (computing device) which controls the frequencies generated by the electromagnetic measuring device and which causes the electronic emulator to produce the complex impedance characteristics of the material under test at the test frequency. Various particular embodiments of the present subject matter include an electronic material impedance emulation circuit that is self-contained, to sense the operating characteristics of the electromagnetic measurement device signal, and to transmit a return signal that emulates the return signal that would occur if the signal were passing through a material under test. The resultant electromagnetic response data of the measuring device is stored in a form that is amenable for communication to a local or remote processor to determine the calibration or standardization of the measuring device.

The present subject includes apparatuses, systems, methods and programs for emulating electrical impedance characteristics of a material having a known electromagnetic response to an electromagnetic field over the full range of operating frequencies for the standardization and calibration of electromagnetic measuring devices.

A first aspect includes an electromagnetic emulator system for emulating an impedance response of a material, the system including: an emulator device including an emulator circuit; and at least one computing device coupled with the emulator device and configured to perform actions including: obtaining instructions for selecting a type of the material; obtaining a signal from a sensor device at an obtained frequency, the obtained frequency being one of a single frequency or a frequency range; and emulating the impedance response of the material at the obtained frequency based upon the type of the material and the signal from the sensor device.

A second aspect includes a method of standardizing a sensor device for measuring a characteristic of a material, the method including: obtaining benchmark impedance response data for the material; positioning the sensor device in communication with an emulator system, the emulator system including: an emulator device including an emulator circuit; and at least one computing device coupled with the emulator device; selecting a type of the material; initiating a sensing signal from the sensor device at a sensing frequency, the sensing frequency being one of a single frequency or a frequency range; obtaining a return signal from the emulator system, the return signal based upon the type of the material and the sensing signal from the sensor; and calibrating the sensor device using the return signal and the benchmark impedance response data.

A third aspect includes a computer program product including program code stored on a computer readable storage medium, which when executed by the at least one computing device, causes the at least one computing device to emulate an impedance response of a material by performing actions including: obtaining a complex impedance response of a benchmark sensor device to a test material at a test frequency, the test frequency being a single frequency or a range of frequencies; obtaining instructions for selecting a type of the material; obtaining a sensor signal at the test frequency from a sensor device; and emulating an impedance response of the material based upon the type of the material and the sensor signal from the sensor device at the test frequency.

A fourth aspect includes a system having: at least one computing device for emulating an impedance response of a material by performing actions including: obtaining instructions for selecting a type of the material; obtaining a sensor signal from a sensor over a range of frequencies; and emulating the impedance response of the material based upon the type of the material and the sensor signal from the sensor over the range of frequencies.

A fifth aspect includes a computer program product having program code stored on a computer readable storage medium, which when executed by at least one computing device, causes the at least one computing device to emulate an impedance response of a material by performing actions including: obtaining instructions for selecting a type of the material; obtaining a sensor signal from a sensor over a range of frequencies; and emulating the impedance response of the material based upon the type of the material and the sensor signal from the sensor over the range of frequencies.

A sixth aspect includes a computer-implemented method of emulating an impedance response of a material, the method including: obtaining instructions for selecting a type of the material; obtaining a sensor signal from a sensor over a range of frequencies; and emulating the impedance response of the material based upon the type of the material and the sensor signal from the sensor over the range of frequencies.

A seventh aspect includes an electromagnetic emulator system for emulating an impedance response of a user-selected type of material, the system including: an emulator device including an emulator circuit; and at least one computing device coupled with the emulator device and configured to perform actions including emulating the impedance response of the user-selected material at an obtained frequency based upon the type of the user-selected material and an obtained signal from a sensor device at the obtained frequency.

An eight aspect includes a computer program product having program code stored on a computer readable storage medium, which when executed by the at least one computing device, causes the at least one computing device to emulate an impedance response of a material by performing actions including: emulating an impedance response of a user-selected material based upon a type of the user-selected material and a sensor signal from a sensor device at a test frequency.

Several objects of the presently disclosed subject matter having been stated hereinabove, and which are addressed in whole or in part by the presently disclosed subject matter, other objects will become evident as the description proceeds when taken in connection with the accompanying drawings as best described herein.

DETAILED DESCRIPTION

Figure 1A:
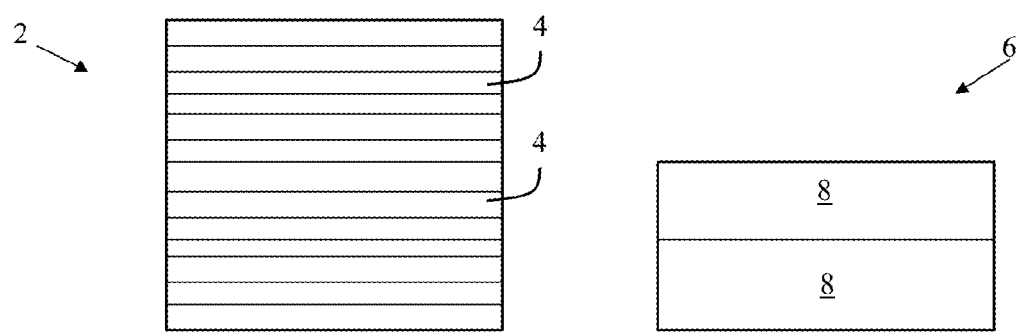
FIG. 1A and FIG. 1B show images of prior art calibration blocks for an electromagnetic measuring device.

The presently disclosed subject matter relates to the standardization and calibration of electromagnetic measuring devices. More particularly, the presently disclosed subject matter relates to apparatus, system, methods and programs for electronically emulating the known complex impedance of a material at a given frequency that is measured by the electromagnetic measuring device.

In this application, "calibration" is defined to mean relating the measured electromagnetic response of the measuring device directly to some physical property of the material under test. "Standardization" is defined as matching the electromagnetic response of the measuring device to the calibration material to that of a "standard" unit such that the response of each unit is identical. The standardization will generally occur before calibration. Both the standardization and calibration are conducted over the range of operating frequencies of the measuring device.

In general, electromagnetic measuring devices will be standardized as part of the manufacturing quality control. Further, in general, electromagnetic measuring devices that are used on asphalt are calibrated such that the electromagnetic response are directly related to the density of the asphalt based upon assigning an equivalent density to the impedance value as measured on a calibration block or produced by the electronic impedance emulator. The electromagnetic response data from two or three of the calibration blocks or impedance values produced by the electronic impedance emulator are related to the asphalt density through a simple linear curve fit with the well known least squares method. The relation of the electromagnetic responses of the measuring device to the properties of soils and concrete are developed through an algorithm based on the measured electromagnetic responses of the measuring devices to control samples of the material under test.

Field measurements of construction materials such as soil, sand, aggregate, asphalt and/or concrete are beneficial in assuring that those materials meet design specifications. For soils, sand, and aggregate, the measurements of interest include the moisture content and the density. For asphalt, the measurement of interest is density. For concrete, the field measurements of primary interest (during concrete pouring) are the amount of free water within the concrete and the amount of hydration that has occurred in the concrete. Conventionally-accepted forms of field measurements include the use of a nuclear density and moisture gauge (NDG) for soils and asphalts, as described in U.S. Pat. No. 2,781,453 and U.S. Pat. No. 3,544,793, both of which are hereby incorporated by reference. Various other destructive measurement techniques have been used conventionally as well. The NDG approach allows for relatively rapid readings in the field, but the NDG devices contain radioactive materials which can cause safety and regulatory concerns. The conventional destructive approaches generally require that the material under test (or MUT) be transported to a laboratory for testing, which entails a time delay.

In view of the shortcomings of the above-noted traditional conventional approaches, more contemporary conventional approaches have focused on methods for conducting field tests on construction materials which provide rapid readings in the field, e.g., in order to assure quality of the construction materials on site. One such contemporary approach is the use of electromagnetic measuring devices which may also entail the use of impedance tomography and impedance spectroscopy. This approach is described in, U.S. Pat. Nos. 5,900,736; 6,414,497; and 7,219,024, each of which is hereby incorporated by reference in its entirety.

Because of variations in manufacturing tolerances, different electromagnetic measuring devices with the same design may not necessarily sense exactly the same values on standardized calibration materials or material under test in the field. Consequently, each sensing probe on the device is individually calibrated at the manufacturing facility, and as a practical matter, the sensing probes should be periodically checked (or recalibrated) to assure that the calibration has been maintained.

For nuclear gauges, calibration is conventionally performed using three large and heavy blocks of material of different densities. Typically, these blocks are aluminum (e.g., 160 lbs/ft$^3$ or pounds-per-cubic-foot), magnesium (e.g., 110 lbs/ft$^3$), and a mix of aluminum and magnesium (e.g., 135 lbs/ft$^3$). Some conventional nuclear calibration devices include shielded capacitance standards, such as those manufactured by Troxler Electronic Laboratories, Inc., and described in U.S. Pat. No. 4,924,173, which is hereby incorporated by reference in its entirety.

As noted herein, electromagnetic measuring devices are typically factory calibrated using two or three large slabs of distinct material, or calibration standards of varying dielectric constants. The size of the calibration material used depends on the size of the sensor to be calibrated and the measurement depth capability of the sensor. Conventionally (e.g., due to commercial availability), the calibration material is approximately 12 to 14 inches wide by 12 to 14 inches long and up to 2 inches thick. The algorithm used to calibrate the device can depend on the type of measuring device that is being calibrated. For single-frequency devices, such as those described in U.S. Pat. Nos. 5,900,736 and 6,414,497, a simple linear curve fit is conventionally used, with a least-squares method applied to the data points for the straight-line equation. For multiple-frequency devices, such as those described in U.S. Pat. No. 7,219,024, various proprietary calibration approaches are used. Regardless of device type, it may be desirable to use a calibration standard that spans the entire range of dielectric values observed in the target material (also referred to as material under test, or MUT).

Figure 1B:
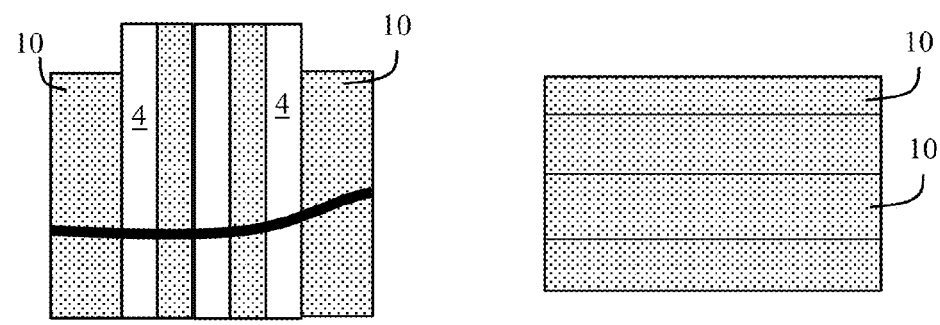
Figure 2:
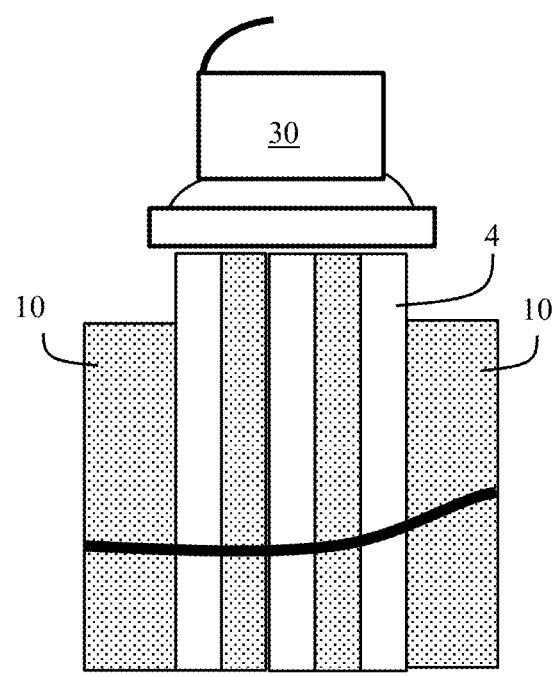
FIG. 2 shows an image of an electromagnetic measuring device in a calibration configuration according to the prior art.

Electromagnetic measuring devices are typically calibrated in a laboratory using bulk homogeneous materials with known electrical properties. These homogeneous materials can include graphite, plastic, nylon, polyvinylchloride, fiberglass reinforced melamine plastic laminates such as NEMA Grade G9 (which will be called G9 hereafter to reflect the whole class of such laminates), glass, and others. As noted herein, these materials are typically used for testing in unit sizes of 12 to 14-inches by 12 to 14-inches stacked to a height of 6 inches, where each test sample can weigh approximately 130 pounds or more. The significant weight of a set of three units (conventionally used for testing) creates a difficulty in the handling and shipment of the units. Additionally, due to the variability of manufacturing the materials, their electrical properties may not be uniform sample-to-sample. This may be particularly true of the G9 material or any other similar laminate. FIG. 1A shows a schematic cross-sectional view of a tall stack 2 (left) of substantially similar dielectric samples 4, and a shorter stack 6 (right) of thicker, substantially similar dielectric samples 8. FIG. 1B shows a set of dielectric samples 4, interposed between sections of a distinct dielectric material 10 (left), and a stack of sections of the dielectric material 10. The number of materials used and types are selected based upon the application of the sensor.

The response of an electromagnetic measuring device to a material under test is related to the electrical properties of the material being tested. Therefore, it is necessary that the calibration standards closely resemble the electromagnetic response of the material under test over the range of frequencies that the measuring device is operating. However, available calibration materials are ineffective in replicating the electromagnetic response of soils or concretes due to the water content in these soils and concretes. As is known in the art, water is a highly polar molecule which goes through a number of "relaxations" over the range of frequencies used by some measuring devices. The heterogeneity of soil combined with significant interfacial effects between the highly polar water molecules and the soil solids surface results in a complex electrical response for which good conventional phenomenological theories do not exist. There are three primary polarization effects in soil: bound water polarization, double layer polarization, and the Maxwell-Wagner (M-W) effect (illustrated in the prior art frequency-permittivity graph in FIG. 3 and FIG. 4). The bound water polarization results from the fact that water can be electrostatically bound to the soil matrix. The degree of binding varies from: unbound or free water at a great distance (>10 molecular diameters); to binding at the matrix surface; to heavily bound, or adsorbed, water.

Figure 3:
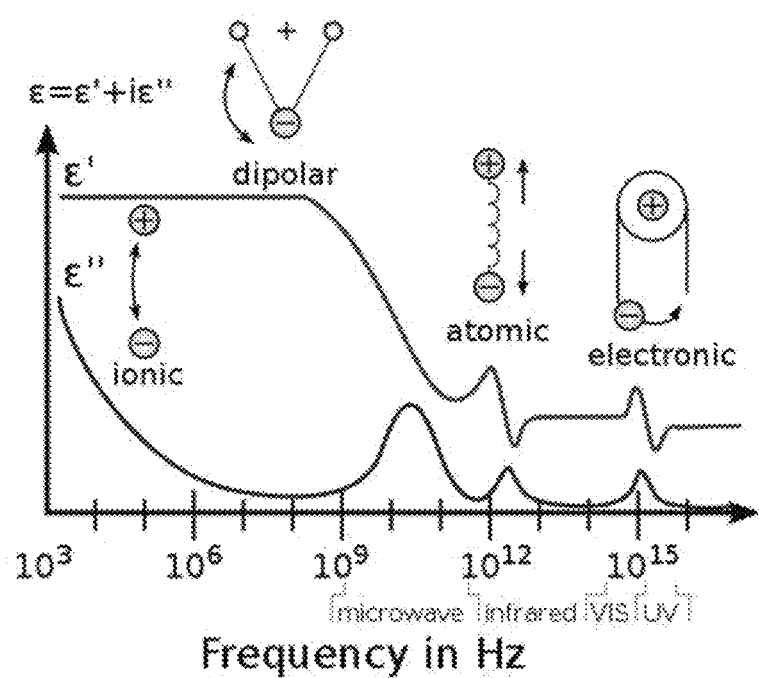
FIG. 3 is an illustration of the dielectric spectrum of an idealized material according to the prior art.
Figure 4:
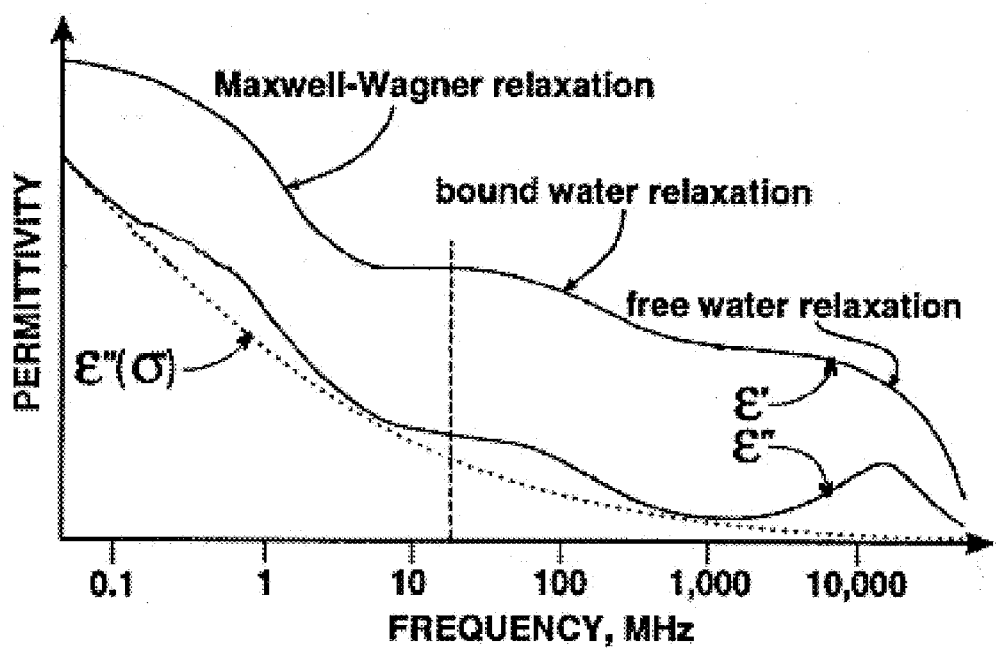
FIG. 4 is an illustration of the dielectric spectrum of a real material (soil) according to the prior art.
Figure 7:
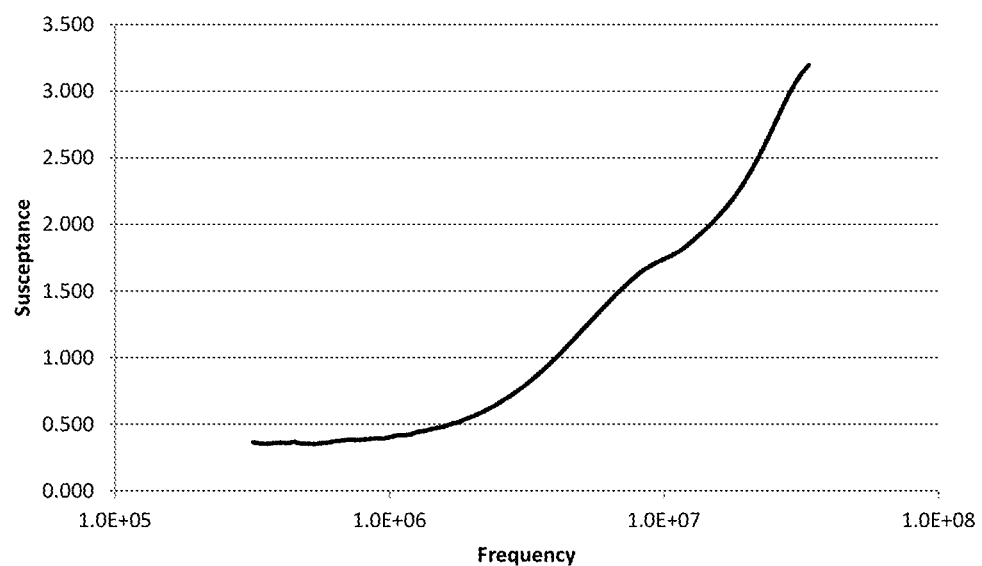
FIG. 7 is a graphical depiction of an example impedance spectrum for a soil obtained using a conventional impedance soil density gauge.
Figure 8:
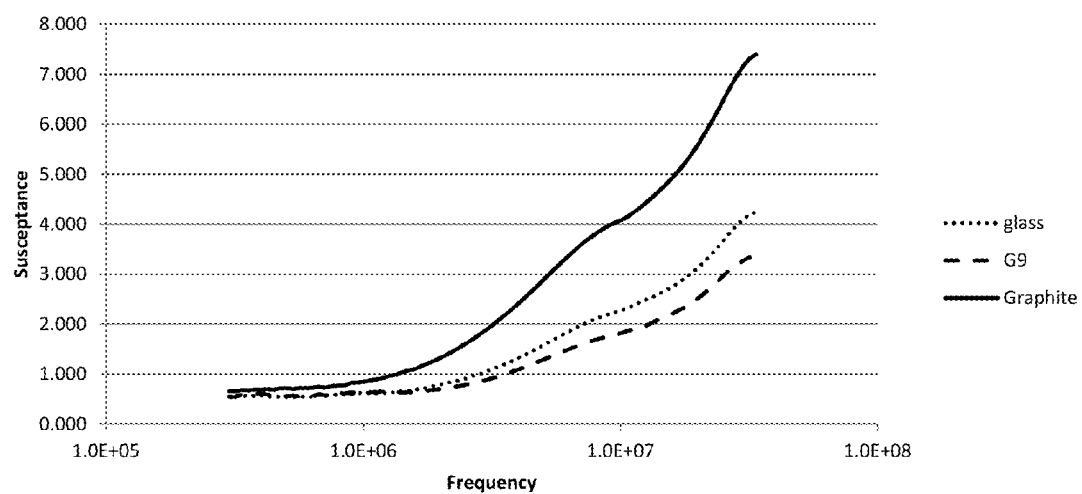
FIG. 8 is an illustration of an example impedance spectrum for conventional calibration materials obtained using a conventional impedance soil density gauge.

The ordinate in FIG. 3 and FIG. 4 is permittivity, which is a property of the material under test. In FIG. 7 and FIG. 8 (described further herein), the ordinate is a measure of the measured impedance, in this case the susceptance, which is the measured effect of the permittivity on the electric field as it passes through the material under test. Permittivity is treated as a complex function (since complex numbers allow specification of magnitude and phase) of the (angular) frequency of the applied field ω, The definition of permittivity therefore becomes:

$$D_0 e^{-i\omega t} = \hat{\epsilon}(\omega) E_0 e^{-i\omega t},$$

Where, $D_0$ and $E_0$ are the amplitudes of the displacement and electrical fields, respectively, and i is the imaginary unit, $i^2 = -1$.

The response of a medium to static electric fields is described by the low-frequency limit of permittivity, also called the static permittivity $\epsilon_S$ (also $\epsilon_{DC}$):

$$\epsilon_s = \lim_{\omega \to 0} \hat{\epsilon}(\omega).$$

At the high-frequency limit, the complex permittivity is commonly referred to as $\in_\infty$. At the plasma frequency and above, dielectrics behave as ideal metals, with electron gas behavior. The static permittivity is a good approximation for alternating fields of low frequencies, and as the frequency increases a measurable phase difference δ emerges between D and E. The frequency at which the phase shift becomes noticeable depends on temperature and the details of the medium. For moderate field strength ($E_0$), D and E remain proportional, and:

$$\hat{\varepsilon} = \frac{D_0}{E_0} = |\varepsilon|e^{i\delta}.$$

Since the response of materials to alternating fields is characterized by a complex permittivity, it is natural to separate its real and imaginary parts, which is done by convention in the following way:

$$\hat{\varepsilon}(\omega) = \varepsilon'(\omega) + i\varepsilon''(\omega) = \frac{D_0}{E_0}(\cos\delta + i\sin\delta).$$

Where: $\in''$ is the imaginary part of the permittivity, which is related to the dissipation (or loss) of energy within the medium; and $\in'$ is the real part of the permittivity, which is related to the stored energy within the medium.

The use of the materials noted herein for standards have been found acceptable by the commercial manufacturers of impedance material characterization gauges for calibration of measuring devices for use on asphalt, which electromagnetically more closely resembles a simple dielectric.

Figure 5A:
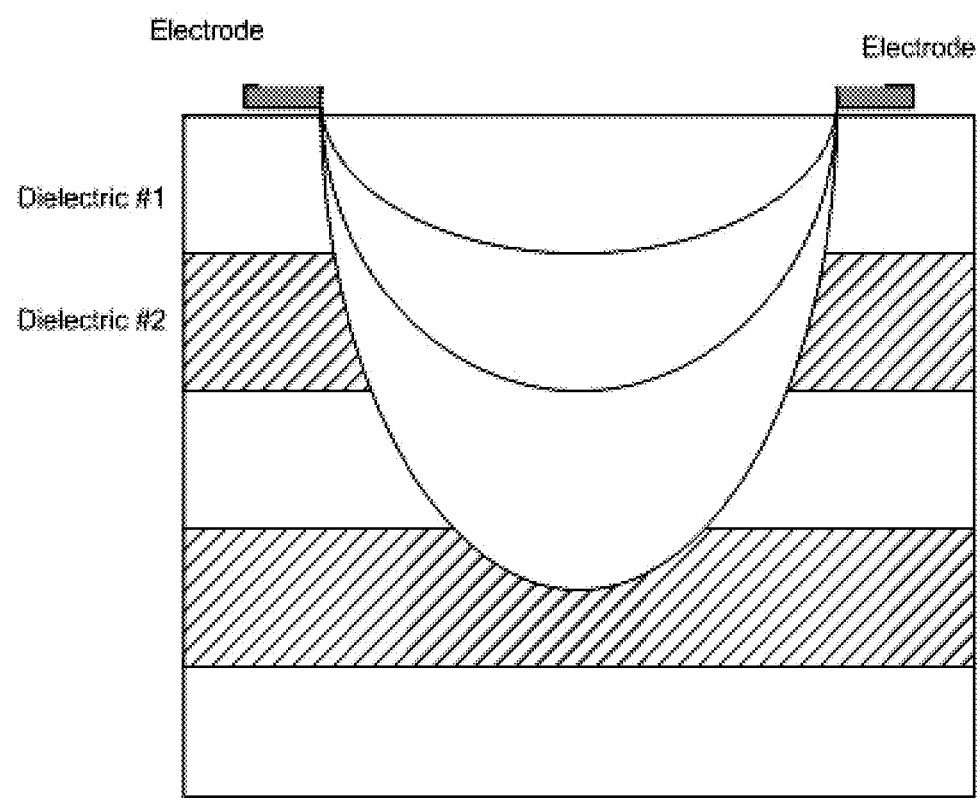
FIG. 5A is a schematic illustration of a stack of dielectric blocks in a calibration configuration, illustrating horizontal electromagnetic field lines.

Another issue in the development of an alternative method of calibration for electromagnetic measuring devices is that the measuring devices are planar measuring devices that emit an electromagnetic field into the material under test or the calibration medium that varies in strength intensity as it penetrates into the material or the calibration medium. This phenomenon is illustrated in the schematic cross-sectional depiction of a multi-level medium including a signal penetration graph 20, as shown in FIG. 5A. Some prior approaches such as those discussed in US Pat. Pub. No 2012/0260736 (incorporated by reference herein in its entirety, suggest that stacking calibration materials of different electrical properties on top of one other, or placing a conductive plate below the calibration material will result in a variation in the electrical properties of the calibration material that aids in the calibration. The inventors of the presently described embodiments have found these approaches ineffective for a number of reasons. First, in the case of stacking blocks of different electrical properties, the block closest to the measuring device's sensor will have a greater influence on the measured properties than materials stacked farther from the sensor. If there is an air gap between the measuring device's sensor and the calibration material (air with a dielectric constant of approximately 1 compared to a material such as G9 with a dielectric constant of approximately 7), the air gap can have a disproportionate impact on the measuring device's calibration. This air gap issue can be alleviated where the measuring device is designed to operate with an air gap as in the system of U.S. Pat. No. 7,219,024 (incorporated by reference herein in its entirety), where the calibration model incorporates the presence of an air gap. It has been found that placing a conductive material below the dielectric calibration material converts the material property measuring device into a capacitive thickness measuring device without a valid calibration of the measuring device.

Figure 5B:
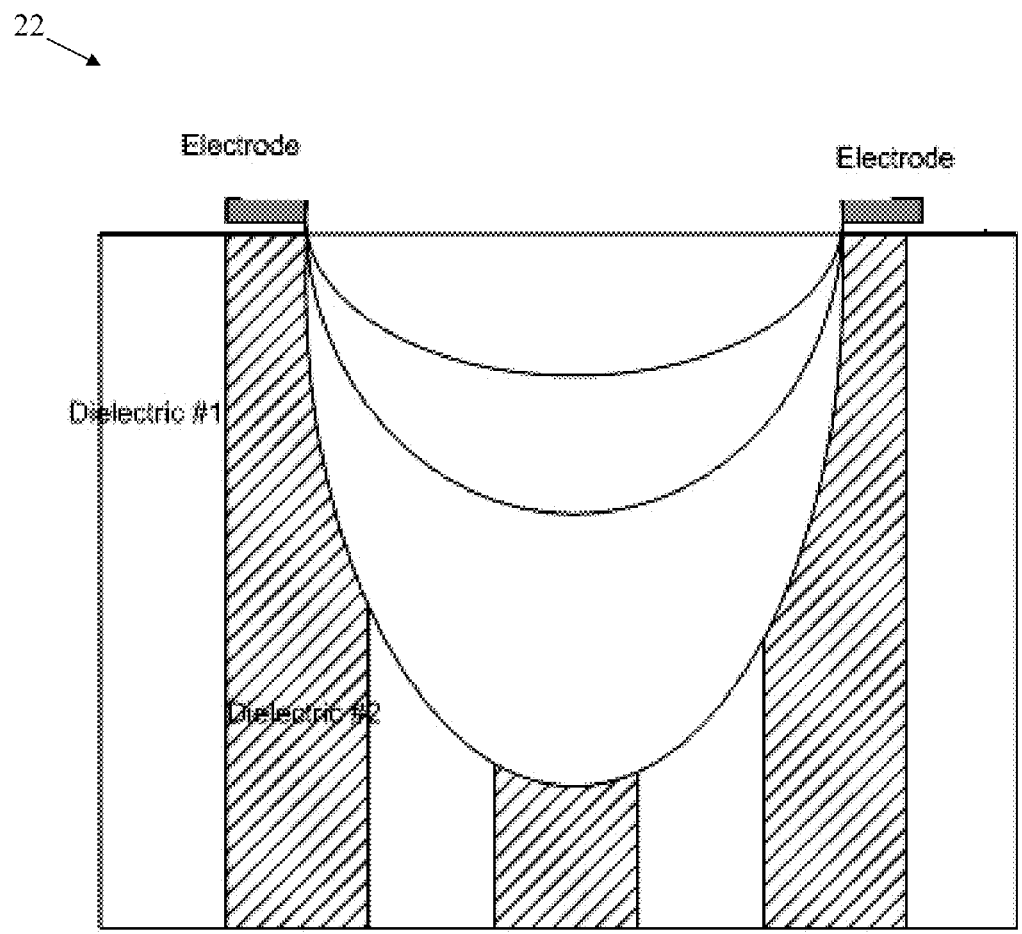
FIG. 5B is a schematic illustration of a stack of dielectric blocks in a calibration configuration, illustrating vertical electromagnetic field lines.

An alternative approach is to create a vertical lamination of the calibration materials as shown in the schematic cross-sectional depiction of a multi-level medium including a signal penetrations graph 22 of FIG. 5B. This alternative approach overcomes some of the shortcomings noted above, but is still deficient when compared with the various embodiments disclosed herein. In particular, this alternative approach still does not account for the fact that solid materials do not replicate the relaxations of water in real materials. The use of fluids according to conventional approaches may increase the range of available dielectric constants, but cannot replicate the relaxations that result from the water in soil or concrete.

An alternate method to replace the current use of materials for the calibration and standardization of electromagnetic measuring devices is the use of an analog equivalent circuit composed of resistors, capacitors and inductors. The use of such an equivalent circuit requires that a circuit model of the measuring device and its interaction with the material under test be converted into a circuit arrangement composed of standard analog components. These equivalent circuits may have value in the design and data analysis of electromagnetic measuring devices. However, their value is limited for the use as a calibration alternative, since the reaction of the signal from the measuring device as it passes through the material under test varies as the frequency changes (See Impedance Spectrum Graph in FIG. 7). With a fixed equivalent circuit, the resultant interaction between the measuring device and the equivalent circuit will be similar to that from a standard calibration material. However, neither the equivalent circuit nor the standard calibration materials account for the various relaxation modes of the water in the material under test.

For at least the herein-noted reasons, the conventional calibration approaches have numerous shortcomings, for example: (1) the size and weight of the calibration material; (2) due to variability in the manufacture of materials currently used, the electrical characteristics vary from sample to sample; and (3) the inability to match the electromagnetic response of calibration materials with intended materials under test over the range of frequencies used by the measuring devices.

In contrast to these conventional approaches, various embodiments of the invention include methods, apparatuses, systems and computer program products for calibrating and standardizing electromagnetic-based measurement devices by effectively emulating the impedance response of desired materials to be tested.

Figure 6:
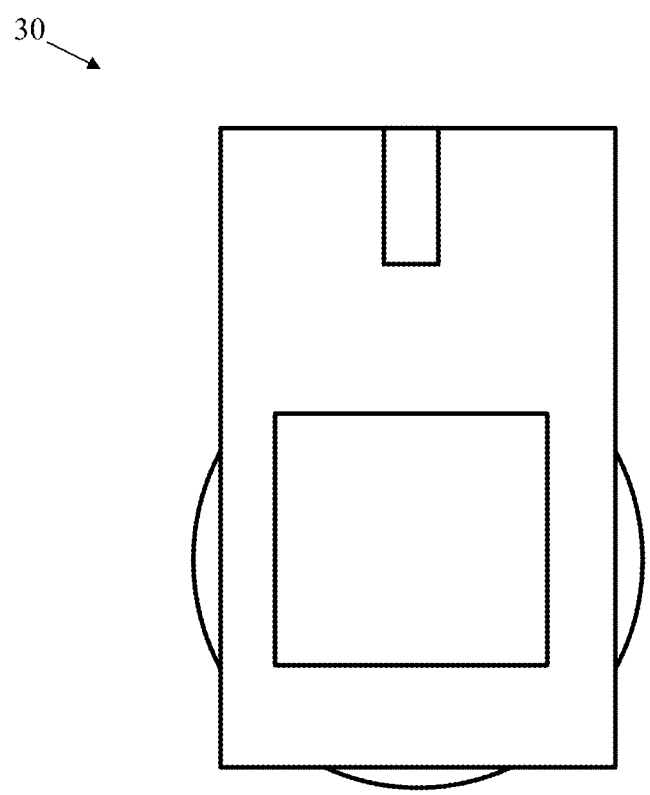
FIG. 6 shows a schematic depiction of an electromagnetic measuring device according to the prior art.

Various embodiments of the invention overcome the deficiencies of conventional approaches by creating artificial dielectrics for use in the calibration and standardization of electromagnetic-based measurement devices. Various embodiments include applying an electronic circuit in communication with the electromagnetic measurement device and emulating the electromagnetic response of a material under test to the electromagnetic field of the measurement device. FIG. 6 shows a schematic plan view of an electromagnetic measuring device 30 that may be used for asphalt or soil testing according to the prior art.

In making measurements and interpreting aspects of the complex impedance with actual impedance measurement devices, it can be helpful to define terms that may be calculated from the output of the measurement device which are the magnitude of the power between the reference signal and the transmit signal that is passed through the material or device under test and the transmitted signal, defined as magnitude, m, and the phase angle, δ, shift between the reference signal and the transmit signal which occurs as the signal passes through the material or device under test. Impedance (Z) is represented mathematically as a complex relation consisting of a real part, resistance, and an imaginary part, reactance:

$$Z=R+iX;$$

Z=the complex value of Impedance;
R=the Resistance; and
X=the Reactance.

Resistance, R, is a material's opposition to the flow of electric current. Reactance, X, is a material's opposition to alternating current due to capacitance (capacitive reactance) and/or inductance (inductive reactance). Susceptance (B) is a complementary representation of the reactance in the term admittance and is defined mathematically as:

$$B=1/X.$$

The Susceptance may be computed from the measured properties as follows:

$$B=\text{the Susceptance}=m^*\sin\delta.$$

Admittance (Y) is a complex quantity which is the inverse of Impedance, and results in the definition of the terms of Conductance and Susceptance:

$$Y=1/Z=G+iB=\text{Admittance}.$$

The Conductance may be computed from the measured properties as follows:

$$G=\text{the Conductance}=m^*\cos\delta.$$

The quantities that are measured by an impedance measurement device are the magnitude and the phase. These quantities are used to compute impedance values such as the susceptance and conductance. FIG. 7 illustrates the typical impedance spectrum characteristics as the computed value of susceptance from soil with a commercial soil density gauge. In FIG. 8, similar spectra of the susceptance are shown from typical materials currently used for calibration and standardization. In FIG. 7 and FIG. 8, the ordinate is an indicator of the measured impedance, in this case the susceptance, which is the measured effect of the permittivity on the electric field as it passes through the material. On inspection of the spectra from the calibration materials and that from soil, it may be observed that the current calibration materials do not closely match that of the actual material under test. As noted herein, various embodiments disclosed overcome these shortcomings in conventional calibration approaches.

Figure 9:
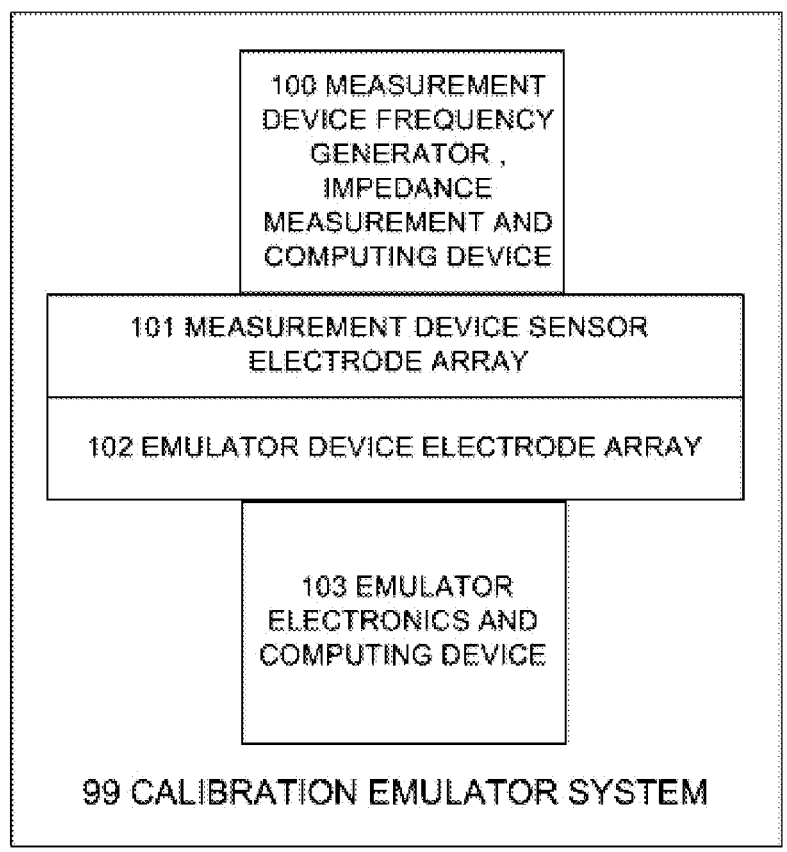
FIG. 9 is a schematic illustration of an emulator system, for application to an electronic impedance emulator with a planar electromagnet, according to various embodiments.

Referring to FIG. 9, one aspect of the disclosure is shown in the schematic depiction of an electromagnetic measuring device calibration system (or simply, calibration emulator system 99). The calibration emulator system 99 can include a measuring device (measurement device frequency generator, impedance measurement and computing device) 100, which includes: a signal generator for generating an electromagnetic field over a range of frequencies; a signal analyzer for measuring the impedance of the material under test; and a computing device for converting the impedance data into meaningful data, e.g., for a user, and/or analysis program to interpret, displaying that data to the user, storing that data in a storage system, etc. The calibration emulator system 99 can further include a sensor electrode array (measurement device sensor electrode array) 101, which includes at least one electrode for transmitting a signal and at least one electrode for receiving a signal, e.g., a return signal. The calibration emulator system 99 can further include an electronic impedance emulator electrode array (emulator device electrode array) 102, which includes an electrode array that mirrors the sensor electrode array 101 as discussed further herein. The calibration system 99 can further include an emulator computing system (emulator electronics and computing device) 103, which can include electronic components for the impedance emulation and a computing device to control the configuration of the electronic components to produce the desired impedance response based upon a real-time operating frequency of the electromagnetic measuring device.

In various embodiments, the emulator device electrode array 102 performs two functions. First, the emulator device electrode array 102 acts as a signal detector which detects the electromagnetic signal transmitted by the sensor electrode array 101, and transmits information about that signal to the emulator computing system 103 for processing. Second, the emulator device electrode array 102 acts as a mirror electrode to those electrodes in the sensor electrode array 101, as further discussed herein.

Figure 10:
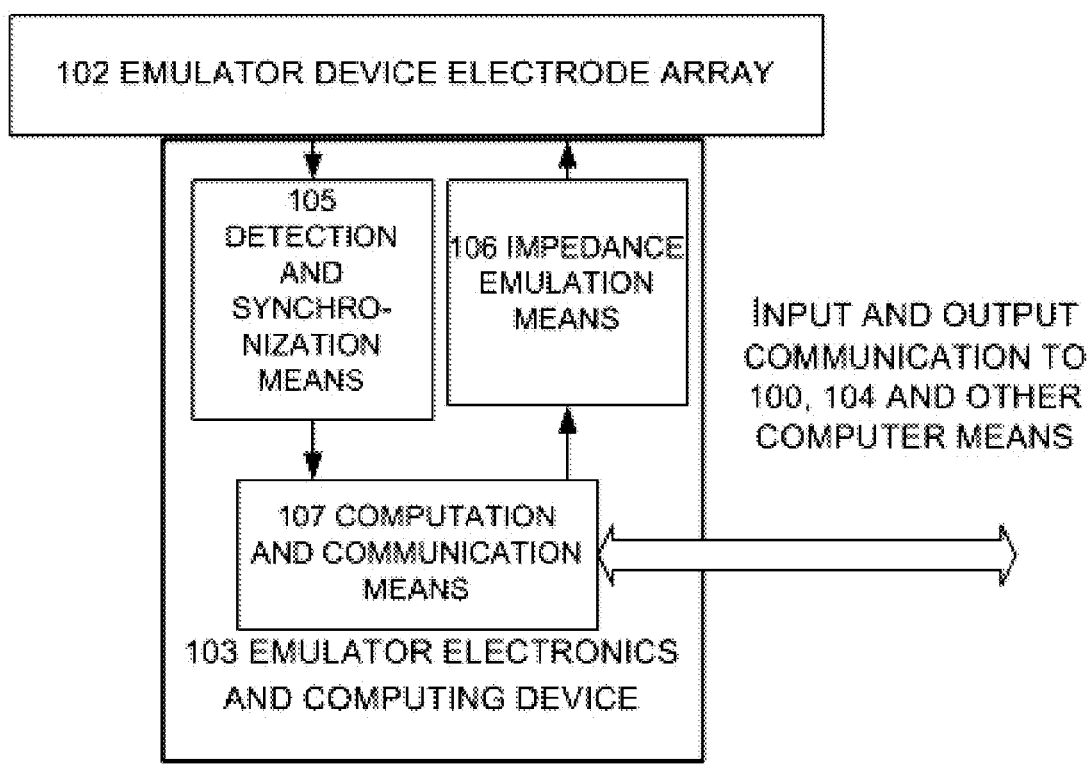
FIG. 10 is an illustration of an emulator and a computing device according to various embodiments.

In various embodiments, the emulator computing system 103 performs several functions. FIG. 10 is a schematic depiction of the emulator computing system 103 and its subcomponents in a data flow diagram with the emulator device electrode array 102. As shown, the emulator computing system 103 includes a detection and synchronization component (means) 105 for receiving the signal information from the emulator device electrode array 102. The detection and synchronization component 105 can communicate the frequency and power level of the signal being generated to a computation and communication component (means) 107. The computation/communication component 107 can then utilize the frequency and power level data to determine the appropriate form of the impedance emulation that should be provided. This computation/communication component 107 can determine the desired value of impedance emulation using a table look-up method or a computation based-method using an established algorithm. Referring back to FIG. 7, the desired value of impedance emulation may be determined by comparing the operating frequency of the measurement device to a standard impedance spectrum for the material to be measured. The values of magnitude, phase, and/or susceptance selected as the standard may be determined as a function of the operating frequency. The magnitude, phase and/or susceptance can be used to control an impedance emulation component (means) 106. The computation and communication component 107 can communicate information about the emulation process to a remote computation device, such as a controlling computing device (alternate controlling computing device) 104 as shown and described with reference to FIG. 13, for storage and further processing. In various alternate embodiments discussed herein, the controlling computing device 104 can also communicate with the measuring device 100, e.g., via wireless and/or hard-wired means.

With reference to FIG. 9 and FIG. 10, in various embodiments, the electromagnetic measuring device calibration system 99 operates using an embedded calibration routine. The emulator computing system 103 and its electrode array 102 can detect, replicate and return a signal with programmed amplitude and phase adjustments. In some cases, the calibration routine may be slowed to grant ample time for detection, replication and signal return. In contrast to conventional approaches, the emulator computing system 103 and its electrode array 102 can determine the frequency of the output signal from the sensor electrode array 101 (FIG. 9) without external information, e.g., without programming or inputting the signal data into the emulator computing device 103. That is, the transmitted signal from the sensor electrode array 101 is automatically detected by the emulator device electrode array 102, and processed by the emulator computing device 103. In various embodiments, a process can include only providing information about a type of the electromagnetic measuring device prior to performing the calibration process. In these embodiments, it may only be necessary to communicate (e.g., manually input, program, wirelessly transmit data, etc.) to the impedance emulator the type of electromagnetic measuring device 100 being calibrated (e.g., a product ID or code), and the type of material intended to be emulated (e.g., concrete, gravel, etc.).

Figure 11:
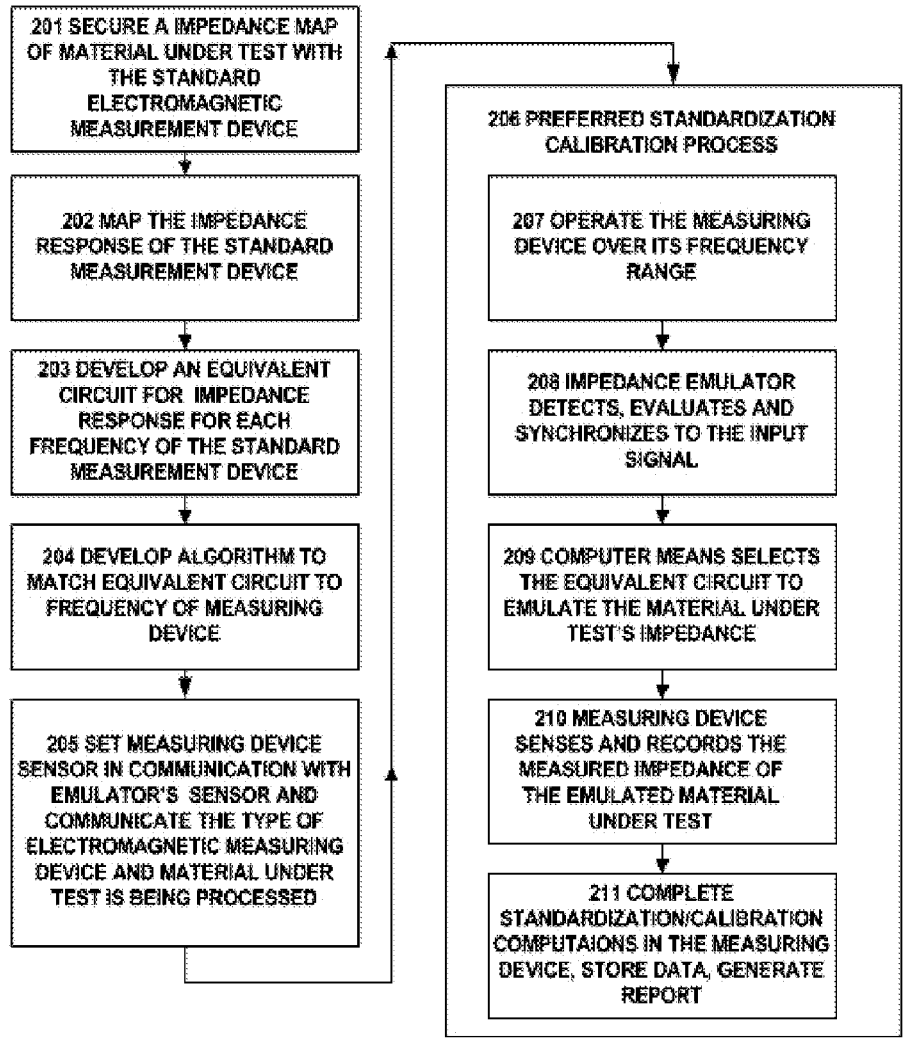
FIG. 11 is the logic flow diagram illustrating operation of an electronic emulator in conjunction with an electromagnetic measuring device, according to various embodiments.

FIG. 11 shows an example operational flow diagram illustrating calibration processes according to various embodiments of the disclosure. The calibration process can begin by obtaining an impedance map that illustrates relationships between the electromagnetic measuring device and the material(s) under test (Process 201). This map can be transformed into a tabulation or plot of the complex impedance response as a function of applied frequencies (Process 202). The measurement device used in Process 201 could be an industry-standard device used as a standard for all other devices of the same design. For example, a standard, or benchmark impedance spectrum may be developed by using a standard (benchmark) measurement device and a standard sample of the material to be tested and emulated. This spectrum data can include, e.g., a table of the measured magnitude and phase at each operating frequency. This table may be used as the standard impedance spectrum from which other spectra are measured, e.g., for other processes described herein. In other embodiments, a measure of the resultant impedance, such as the susceptance shown in FIG. 7, may be used as the standard impedance spectrum. The next process, P203 can include developing an equivalent circuit (e.g., circuit algorithm) to match the impedance response of the benchmark measurement device to the material under test (MUT) over the frequency range of the measuring device. The replicated received signal can be attenuated by a defined amount, and phase delayed by a defined amount. These two adjustments (attenuation and delay) can be performed digitally, in the process of replicating the signal. Next, in process (P204), a control algorithm can be used to control matching of the equivalent circuits with the frequencies generated by the measuring device. The control algorithm may be derived according to various embodiments, or may be developed prior to process P204 in other embodiments. In process (P205), the electrode sensor array of the measurement device (101) is placed in communication with the electrode sensor array (102) of the electronic emulator. The desired impedance response to the MUT is communicated to the computing means of either the measurement device, the electronic emulator or both. This process (P205) can also include entering data about the type of measuring device being calibrated and the material under test into the calibration system.

In various embodiments, standardization and calibration is conducted in process P206, which includes sub-processes P207-P211. In sub-process P207, the measuring device is initiated and cycled over its full operating frequency range. In sub-process P208, the emulator device detects, evaluates and synchronizes to the current operating frequency of the measuring device. The computing device (means) can then select the equivalent circuit most appropriate to emulate the material based upon the operating frequency in process P209. That is, the computing device selects an appropriate change in amplitude and phase of the measuring signal based upon the response of the material under test at the frequency of operation of the measuring device. In sub-process P209, the emulator generates a signal that has the appropriate change in amplitude and phase at the matched transmitted frequency to emulate the signal as if it were transmitted through the standard test material by the standard gauge. After detecting and recording the measured impedance of the emulated material, the measuring device can complete the standardization and/or calibration of the process P210, e.g., by embedding the standardization and/or calibration data in the calibration system's computing device. The calibration data can be stored in the calibration system computing device, and can be made available for transmission/retrieval to/by a remote computing system for further analysis and/or data base manipulation (process P211).

Figure 12:
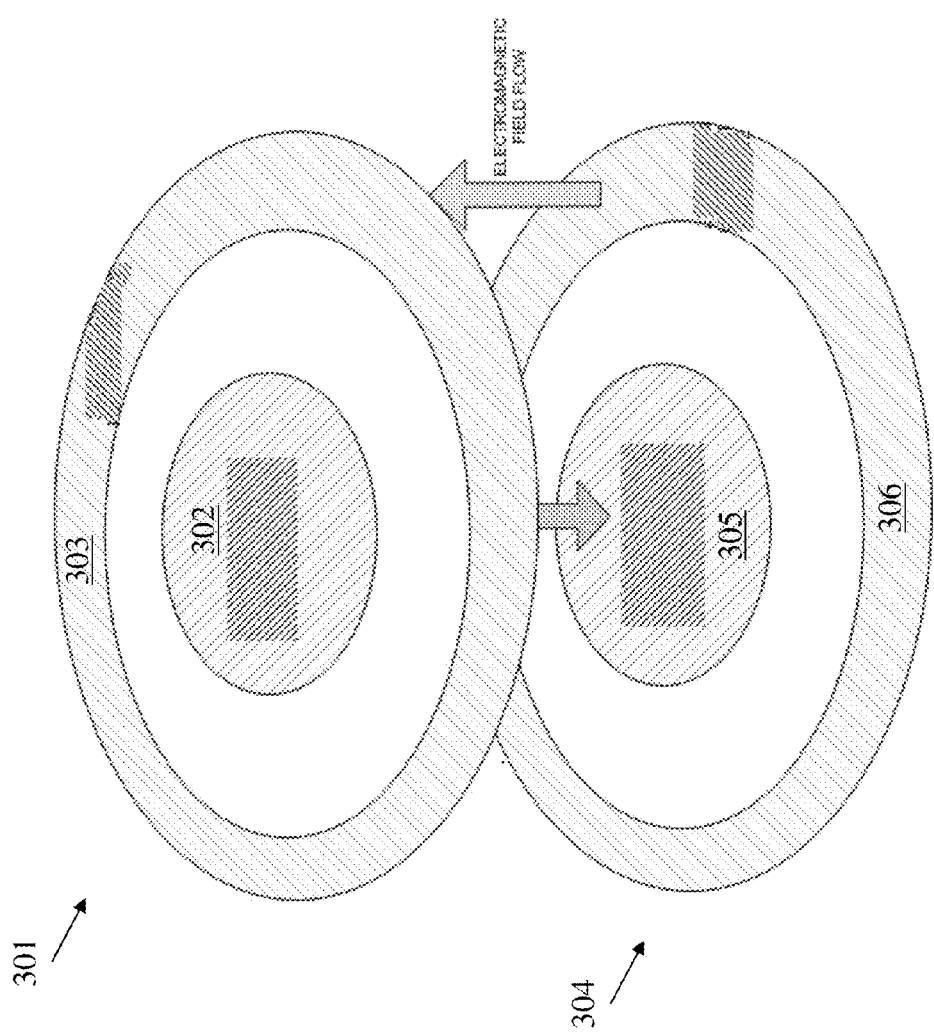
FIG. 12 is a schematic illustration of an electrode matching an electronic emulator to an electromagnetic measurement device, with planar sensors not in electrical communication, according to various embodiments.

The sensor electrode design of the electronic impedance emulator mirrors that of the electromagnetic measuring device. This can be seen in the example schematic electrode design shown in FIG. 12. FIG. 12 depicts an electromagnetic measuring device sensor electrode array 301 including a central circular electrode (302), which is the high (transmitting) electrode surrounded, by a ring electrode (303) which is the low (receiving) electrode. The electronic impedance emulator sensor electrode array (304) is a mirror image if the electromagnetic measuring device sensor 301, including a central circular electrode (305) which is the low (receiving) electrode, surrounded by a ring electrode (306), which is the high (transmitting) electrode. This arrangement allows for the field, voltage or current to flow continuously from the measuring device electrode 301 to the ring electrode 303. As shown in this embodiment, the two arrays 301, 304 may be physically separated from one another. Depending on the type and design of the electromagnetic measuring device, the sensors arrays 301, 304 may be physically isolated from one another (not physically contacting each other), electrically isolated from one another, or physically and/or electrically connected to one another.

Figure 13:
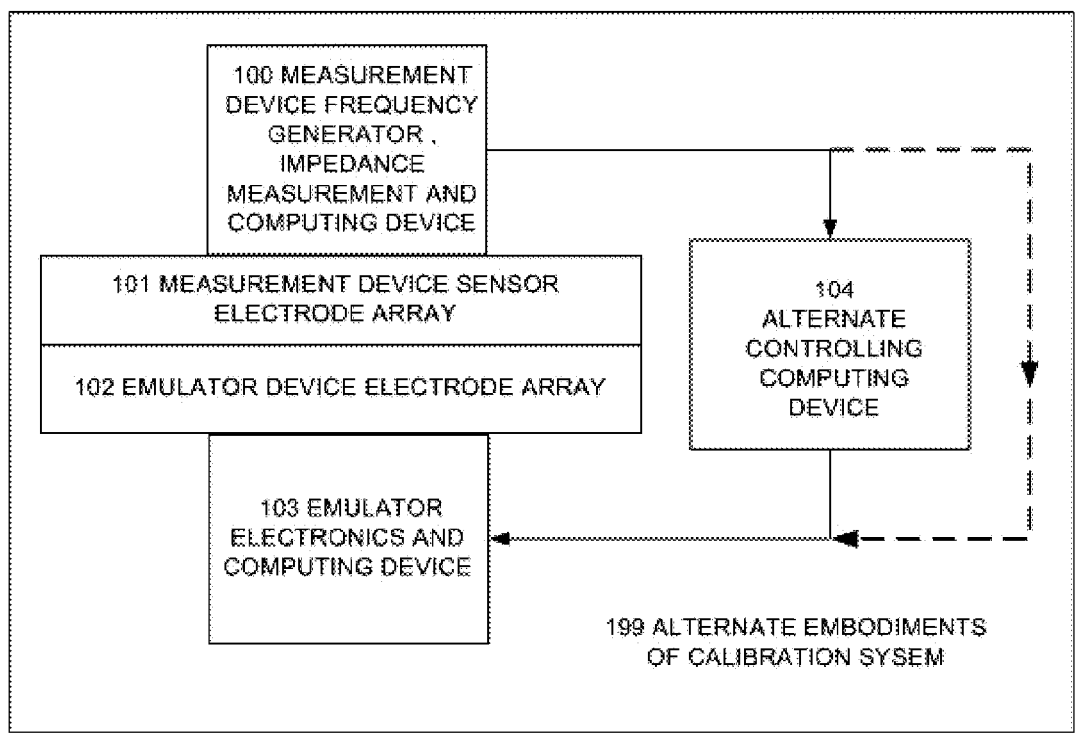
FIG. 13 is an illustration an alternate system configuration, for application to a planar sensor, according to various embodiments.

An alternate embodiment of a calibration system 199 according to various embodiments of the disclosure is illustrated in the system/data flow diagram of FIG. 13. As in various other embodiments described herein, the calibration system 199 can include a measuring device 100, and a measurement device sensor electrode array 101, which includes a sensor electrode array (as discussed with reference to FIG. 9). The calibration system 199 also includes the emulator device electrode array 102, which is an electrode array configured to mirror the array 101 as discussed herein. The emulator computing system (or, computing device) 103 can include electronic components for the impedance emulations and a computing device to digitally control the electronic components to produce the desired impedance response at the current operating frequency of the electromagnetic measuring device 100. However in this alternate embodiment, the electromagnetic measuring device 100 and the emulator computing system 103 are operably connected with a (alternate) controlling computing device 104. In various embodiments, the controlling computing device 104 is embedded in the measuring device 100 or the emulator computing system 103. Alternately, the controlling computing device 104 can include an independent computing device which communicates with the electromagnetic measuring device 100 and the emulator computing system 103. In either case, the controlling computing device 104 can communicate with the electromagnetic measuring device 100 and the emulator computing system 103 in order to perform the calibration functions described herein.

Figure 14:
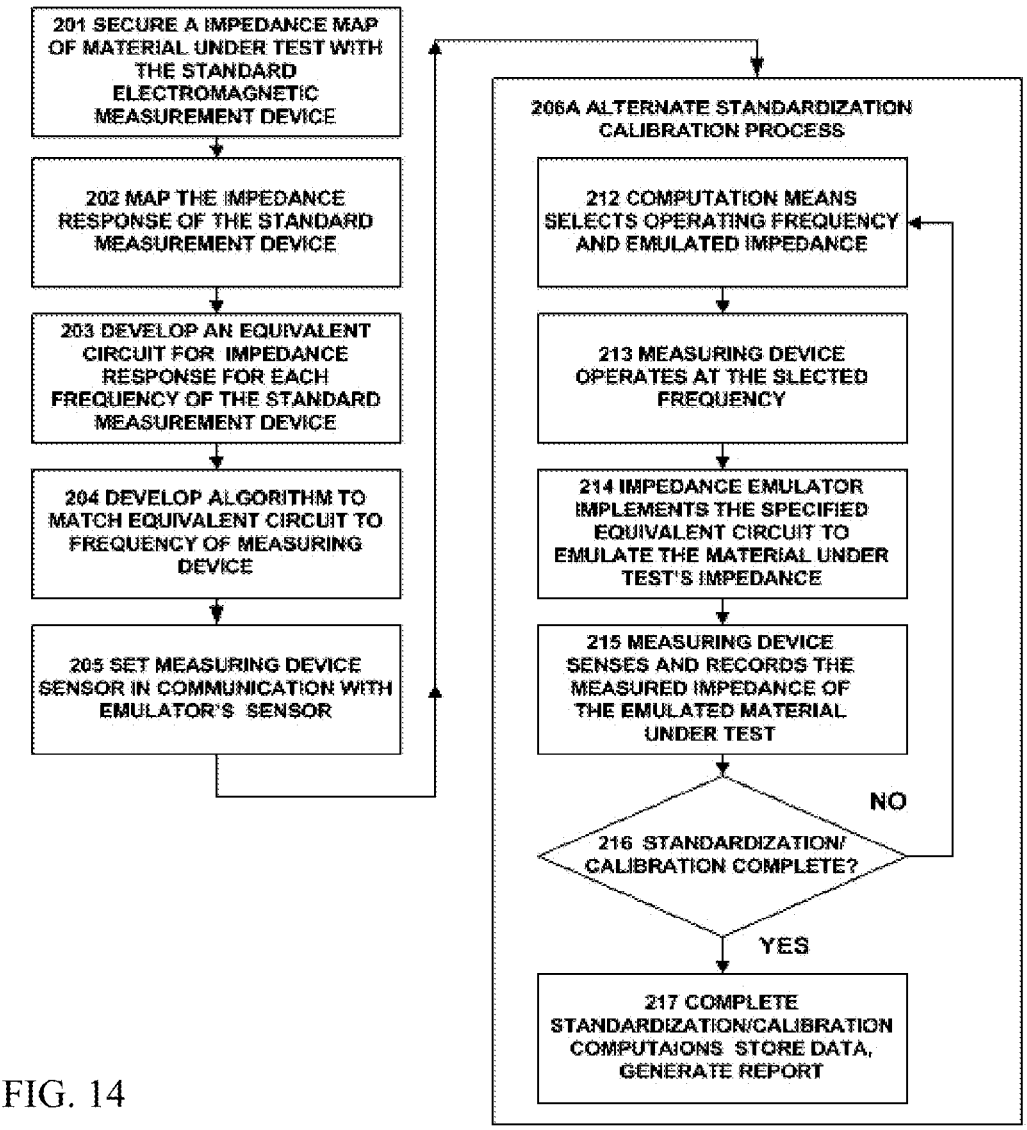
FIG. 14 is a logic flow diagram depicting processes performed by an electronic impedance emulator with and electromagnetic measuring device, according to various embodiments.

The operation logic flow for various alternative embodiments is shown in the flow diagram of FIG. 14. As compared with the process flow in FIG. 11, processes P201 through P205 can be substantially identical, however, following process P205, process P206A includes an alternative scenario. Process P206A can include a plurality of sub-processes, including sub-process P212, where the controlling computing device 104 (FIG. 13) selects the operating frequency for operation of the measuring device (including measuring device 100 and electrode array 101, FIG. 13). The measuring device (including measuring device 100 and electrode array 101) then operates at the selected frequency (process P213). The impedance emulator device (including emulator electrode array 102) detects, evaluates and synchronizes to the current operating frequency of the measuring device (measuring device 100 and electrode array 101) (sub-process P213). In sub-process 214, the emulator (including emulator electrode array 102 and emulator electronics/computing device 103) implements a specified equivalent circuit to emulate the impedance of the selected material (material under test). More specifically, the emulator (emulator electrode array 102 and emulator electronics/computing device 103) generates a signal that includes corresponding changes in amplitude and phase at the matched transmitted frequency to emulate the return signal though it were transmitted through the standard test material by the standard gauge.

The changes in magnitude and phase made to the return signal may be provided by the computing device (computing device 104) in sub-process P214, or can be stored in the computing device 103 within the emulator device. The measuring device (including measuring device 100 and sensor array 101) senses and records the measured impedance (return signal) of the emulated material under test in sub-process P215. In some cases, a test is run to determine whether the standardization is complete (Decision D216). That is, the computing device 104 determines whether all frequencies in the operating frequency range have been emulated. If not (No to Decision D216), sub-processes P212-P215 are repeated with a distinct frequency (e.g., a next frequency, or adjacent frequency) in the operating range of the measuring device (measuring device 100 and sensor array 101). If the operating range of frequencies is completed (Yes to Decision D216), the standardization/calibration is complete and the calibration data is stored in the computing device 100 on the measuring device (process P217). In some cases, the calibration data and a report are generated which may then be transmitted, e.g., to a remote computing device for further analysis and/or database manipulation.

Figure 15:
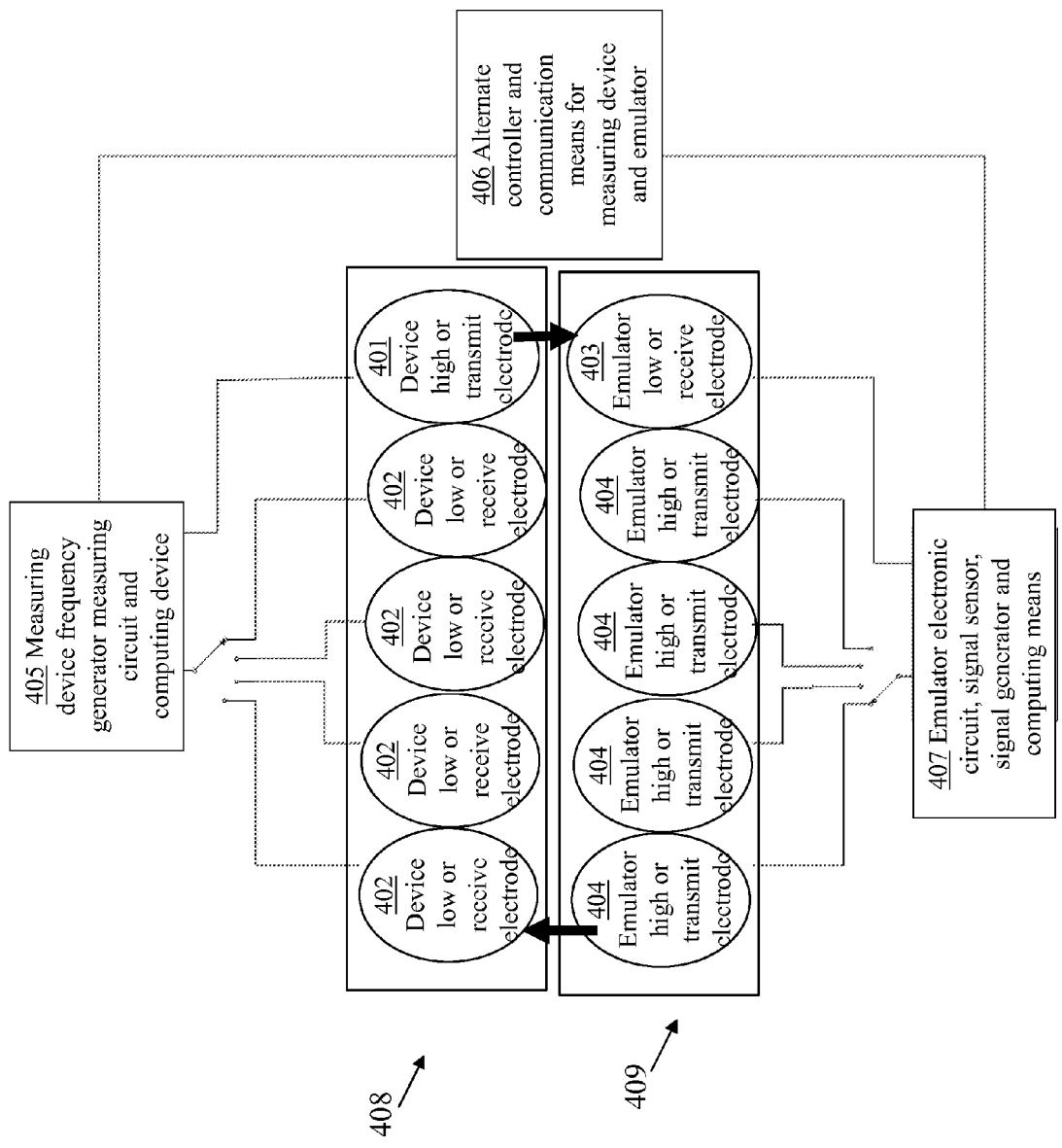
FIG. 15 is an illustration of an alternate system configuration, applied to a linear electrode sensor array, according to various embodiments.

Various alternate embodiments of the present invention are illustrated in the schematic system/dataflow diagram of FIG. 15. In these embodiments, the sensor array 408 in the measuring device can include a planar linear electrode array in which the electrodes may be either a transmitter or receiver. In this illustration, the measuring device can include an electrode which is the high (or transmitting) electrode (401) in communication with the emulator's low (or receiving) electrode (403) on the sensor array 409 of the emulator. The measuring device's low (or receiving) electrodes 403 may be alternatively any of the electrodes (402) or all of the 402 electrodes simultaneously. These electrodes on the sensor array 408 of the measuring device will be in communication with the high or transmitting electrodes (404) of the emulator's sensor array 409. The emulator electrodes may also alternatively be in communication with the singular or all active measuring device electrodes (402). The measuring device includes a computing device (405) to generate the electromagnetic signal at the selected frequencies and to measure the signal that passes through the material under test compared to the reference transmitted signal. The computing device 405 can calculate the desired physical properties of the material under test and make the data about those physical properties available, e.g., to a user or other computing device.

The emulator system includes a computing device (computer means) (407) to obtain the signal from the measuring device (via electrode arrays 408, 409) and a computing device to relate the obtained signal(s) to the desired response that would be obtained by the material under test with a benchmark measuring device. The emulator system can also include electronic circuitry to produce the signal that matches the desired impedance response of the material under test.

The illustrated system in FIG. 15 includes an optional computing device (controller/communication device) (406) that can communicate with both the measuring system computing device 405 and the emulator system computing device 407.

Figure 16:
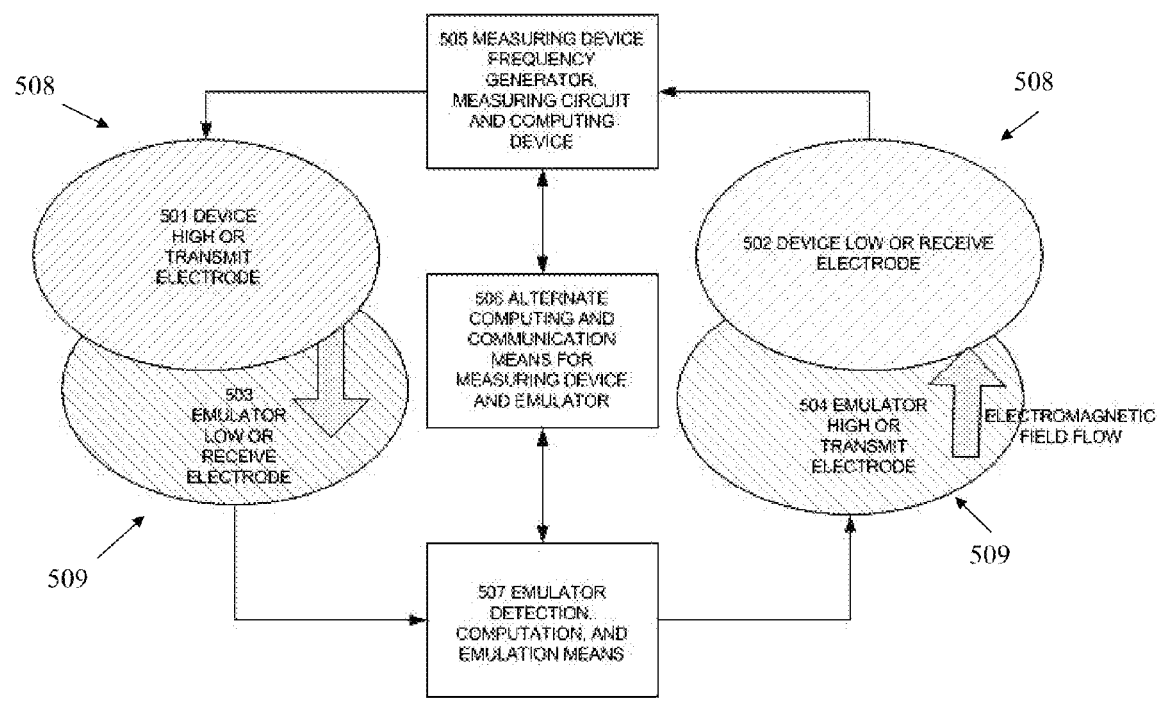
FIG. 16 is an illustration another system configuration, applied to a non-planar sensor, according to various embodiments.

Alternate systems according to various aspects of the disclosure are illustrated in the schematic diagram of FIG. 16. In these embodiments, a sensor array 508 on the measuring device, and/or a sensor array 509 on the emulator device, can include a non-planar sensor array. In this illustration, the measuring device array 508 can include a high (or transmitting) electrode (501), a low (or receiving) electrode (502), and a signal generator (e.g., a device for generating an electromagnetic field over a range of frequencies). The measuring device can further include a measurement device (e.g., signal receiver/analyzer) for measuring the impedance of the material under test (as impedance data), and a computing device configured to convert the impedance data into physical measurement parameters, such as density and moisture, data for the use and/or display to the user. Collectively, these components form the measuring device's computing device 505. This computing device 505 can communicate data to other computer system(s) for storage and analysis.

As shown, the (electronic impedance) emulator system can include a low (receiving electrode) (503), a high (or transmitting electrode) (504), and an electronic emulator system 507, which can include electronic components performing impedance emulation, and a computing device (as described with respect to any computing device(s) herein) to control the configuration of those electronic components to produce the desired impedance response at the current operating frequency of the electromagnetic measuring device. Also shown, according to various alternative embodiments, the emulator system can include a controller and communication device 506, which can include a computing device that communicates with the measuring device computing device 505 and the emulator system 507. The controller and communication device 506 can communicate operating condition data about the measuring device computing device 505 to the emulator system 507. This operating condition data can aid the emulator system 507 to produce the desired impedance response to a sensor signal from the measuring device. It is also possible to have a direct connection between the measuring device computing device 505 and the emulator system 507, as illustrated in the dashed-line connection in FIG. 13.

In a non-planar electromagnetic device, e.g., as shown in FIG. 16, individual electrodes (e.g., receiving electrode 503 and transmitting electrode 504; and receiving electrode 502 and transmitting electrode 501) are physically separated from one another and not necessarily oriented in the same plane. In the standardization and calibration process described herein, the measuring device electrodes (501, 502) may have any orientation as long as their mode of communication with the emulator electrodes (503, 504) are the same during operation, e.g. in non-conductive contact, physically disconnected, or in conductive contact with one another.

Figure 17:
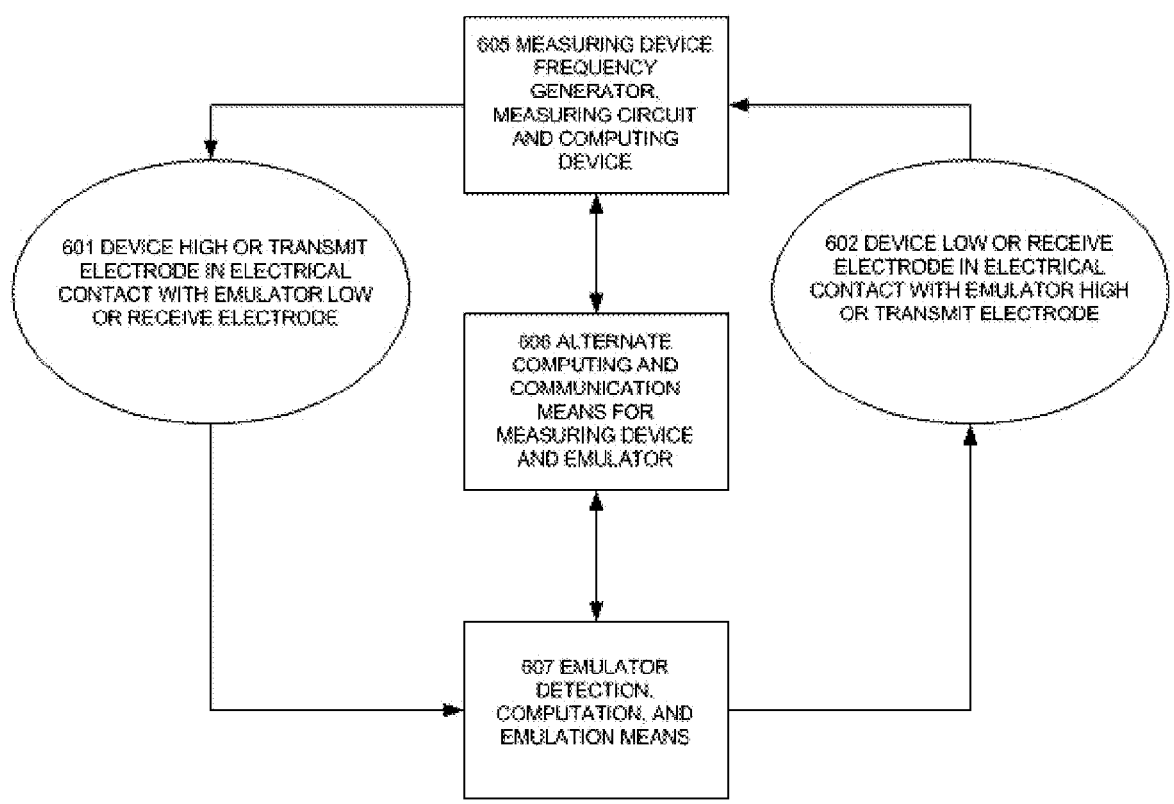
FIG. 17 is an illustration an alternate system configuration, applied to a planar sensor with electrical contact between the sensor and the material under test, according to various embodiments.

Various additional embodiments are illustrated in the schematic data-process flow diagram of FIG. 17. In these embodiments, the sensor(s) of the electromagnetic measuring device are in electrical contact with the material under test. The operation in these embodiments can be similar to that described with respect to FIG. 16, with a distinction being that the high (transmitting) electrode of the measuring device (601) is electrically connected to the low (receiving) electrode of the emulator (602). The system can include a measuring device signal generator/analyzer/computer system (or simply, measuring device computing device) 605, which can be configured to: generate an electromagnetic signal field over a range of frequencies; measure the impedance of the material under test after transmission of the electromagnetic signal field; and/or convert the impedance data into interpretable data, e.g., for display to a user, storage, transmission, etc. The system can further include an electronic emulator system 607, which can include electronic components configured to emulate impedance functions, as well as a computing device configured to control the configuration of the electronic components to produce the desired impedance response at the current operating frequency of the electromagnetic measuring device. The system can further include at least one control system 606 that is configured to communicate with the measuring device computing device 605 and the electronic emulator system 607. The control system 606 can communicate with the measuring device computing device 605 and electronic emulator system 607 about an operating condition of the measuring device computing device 605 in order to aid the electronic emulator system 607 in producing the desired impedance response. It is also possible to utilize a direct connection between the measuring device computing device 605 and the electronic emulator system 607, as illustrated and described with reference to FIG. 13 (dashed-line direct connection shown).

Various additional embodiments of the invention include systems, computer program products and computer-implemented methods for emulating an impedance response of a material. It is understood that some of the processes in the methods for emulating an impedance response of a material are similar to those described with respect to other embodiments herein. It is further understood that a "computing device" (or multiple "computing devices") as used herein can refer to one or more hardware and/or software components described with respect to any of the embodiments herein.

Figure 18:
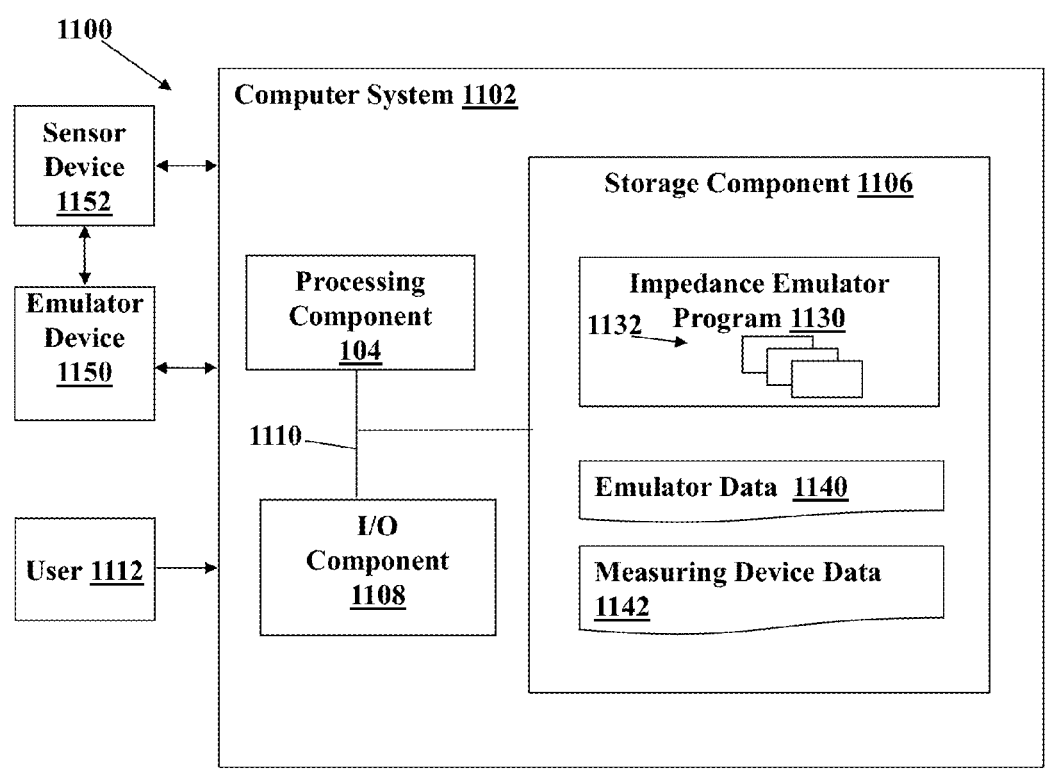
FIG. 18 shows an illustrative environment including an impedance emulator system according to various embodiments.

FIG. 18 depicts an illustrative environment 1100 for emulating an impedance response of a material according to various embodiments. To this extent, the environment 1100 includes a computer system 1102 that can perform a process described herein in order to emulate an impedance response of a material. In particular, the computer system 1102 is shown as including an impedance emulator program 1130, which makes computer system 1102 operable to emulate an impedance response of a material by performing any/all of the processes described herein and implementing any/all of the embodiments described herein.

The computer system 1102 is shown including a processing component 1104 (e.g., one or more processors), a storage component 1106 (e.g., a storage hierarchy), an input/output (I/O) component 1108 (e.g., one or more I/O interfaces and/or devices), and a communications pathway 1110. In general, the processing component 1104 executes program code, such as the impedance emulator program 1130, which is at least partially fixed in the storage component 1106.

While executing program code, the processing component 1104 can process data, which can result in reading and/or writing transformed data from/to the storage component 1106 and/or the I/O component 1108 for further processing. The pathway 1110 provides a communications link between each of the components in the computer system 1102. The I/O component 1108 can comprise one or more human I/O devices, which enable a human user 1112 to interact with the computer system 1102 and/or one or more communications devices to enable a system user 1112 to communicate with the computer system 1102 using any type of communications link. To this extent, the impedance emulator program 1130 can manage a set of interfaces (e.g., graphical user interface(s), application program interface, etc.) that enable human and/or system users 1112 to interact with the impedance emulator program 1130. Further, the impedance emulator program 1130 can manage (e.g., store, retrieve, create, manipulate, organize, present, etc.) data, such as emulator data 1140, measurement device 1142, etc., using any solution.

In any event, the computer system 1102 can comprise one or more general purpose computing articles of manufacture (e.g., computing devices) capable of executing program code, such as the impedance emulator program 1130, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the timing quantity impedance emulator program 130 can be embodied as any combination of system software and/or application software.

Further, the impedance emulator program 1130 can be implemented using a set of modules 1132. In this case, a module 1132 can enable the computer system 1002 to perform a set of tasks used by the impedance emulator program 1130, and can be separately developed and/or implemented apart from other portions of the impedance emulator program 1130. As used herein, the term "component" means any configuration of hardware, with or without software, which implements the functionality described in conjunction therewith using any solution, while the term "module" means program code that enables the computer system 1102 to implement the functionality described in conjunction therewith using any solution. When fixed in a storage component 1106 of a computer system 1102 that includes a processing component 1104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 1102.

When the computer system 1102 comprises multiple computing devices, each computing device may have only a portion of impedance emulator program 1130 fixed thereon (e.g., one or more modules 1132). However, it is understood that the computer system 1102 and impedance emulator program 1130 are only representative of various possible equivalent computer systems that may perform a process described herein. To this extent, in other embodiments, the functionality provided by the computer system 102 and impedance emulator program 1130 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 1102 includes multiple computing devices, the computing devices can communicate over any type of communications link. Further, while performing a process described herein, the computer system 1102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 1102 can obtain or provide data, such as emulator data 1140 (e.g., from an emulator device 1150, similar to emulator devices described herein) and measuring device data (e.g., from sensor device 1152, similar to sensor/measuring devices described herein) 1142 using any solution. For example, the computer system 1102 can generate and/or be used to generate emulator data 1140 and measuring device data 1142, retrieve emulator data 1140 and measuring device data 1142, from one or more data stores, receive emulator data 1140 and measuring device data 1142, from another system (e.g., sensor device 1152, emulator device 1150, etc.), send emulator data 1140 and measuring device data 1142 to another system, etc.

While shown and described herein as a method and system for emulating the impedance response of a material, e.g., for calibrating a sensor, it is understood that aspects of the invention further provide various alternative embodiments. For example, in one embodiment, the invention provides a computer program fixed in at least one computer-readable medium, which when executed, enables a computer system to group windows based on user-defined contexts. To this extent, the computer readable medium includes program code, such as the impedance emulator program 1130 (FIG. 18), which implements some or all of the processes and/or embodiments described herein. It is understood that the term "computer readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the impedance emulator program 1130 (FIG. 18), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for grouping windows based on user-defined contexts. In this case, a computer system, such as the computer system 1102 (FIG. 18), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

It is understood that aspects of the invention can be implemented as part of a business method that performs a process described herein on a subscription, advertising, and/or fee basis. That is, a service provider could offer to group windows based on user-defined contexts as described herein. In this case, the service provider can manage (e.g., create, maintain, support, etc.) a computer system, such as the computer system 1102 (FIG. 18), that performs a process described herein for one or more customers. In return, the service provider can receive payment from the customer(s) under a subscription and/or fee agreement, receive payment from the sale of advertising to one or more third parties, and/or the like.

Various particular embodiments include a system (e.g., computer system 1102) having: at least one computing device for emulating an impedance response of a material by performing actions including:

A) obtaining instructions for selecting a type of the material;

B) obtaining a sensor signal from a sensor over a range of frequencies; and

C) emulating the impedance response of the material based upon the type of the material and the sensor signal from the sensor over the range of frequencies.

In various embodiments, the at least one computing device is further configured to perform the emulating (process C) by further performing actions including:

C1) determining a top of the range of frequencies and a bottom of the range of frequencies from the sensor; and C2) selecting an equivalent circuit configured to emulate the impedance response of the material from the top of the range of frequencies to the bottom of the range of frequencies.

In various embodiments, the emulating (process C) includes providing a return signal including data about a characteristic of the material. In some cases, the return signal is detectable by the sensor.

According to various embodiments, the at least one computing device is coupled with an emulator electrode array, which can include a set of electrodes configured to obtain the sensor signal.

In various embodiments, the process of emulating (process C) includes providing a return signal including data about a characteristic of the material, and the set of electrodes are further configured to transmit the return signal, e.g., for detection by the sensor.

In some embodiments, the set of electrodes is configured to perform at least one of the obtaining of the sensor signal or the providing of the return signal without physically contacting the sensor. That is, in some embodiments, the set of electrodes are physically separated from the sensor.

In various embodiments, the at least one computing device is further configured to perform the following processes:

D) mapping an impedance response of a benchmark electromagnetic device for the material over the range of frequencies;

E) developing an equivalent circuit model representing the impedance response of the material for each frequency over the range of frequencies; and F) developing an equivalent circuit matching algorithm matching the equivalent circuit model with a corresponding one of the frequencies over the range of frequencies.

In various embodiments, the at least one computing device is further configured to obtain an impedance map indicating the impedance response of the material as determined by the benchmark electromagnetic measurement device.

In various additional embodiments, an electromagnetic emulator system (e.g., system 1100, FIG. 18) for emulating an impedance response of a user-selected type of material includes: an emulator device (emulator device 1150, FIG. 18) including an emulator circuit; and at least one computing device (e.g., computer system 1102 having impedance emulator program 1130, FIG. 18) coupled with the emulator device and configured to perform actions including emulating the impedance response of the user-selected material at an obtained frequency based upon the type of the user-selected material and an obtained signal from a sensor device at the obtained frequency.

In various particular embodiments, the emulating includes generating a return signal that emulates the impedance response (of the user-selected material) and is detectable by the sensor device (e.g., sensor device 1152).

In some particular embodiments, the emulator device includes a set of electrodes including: a) a receiving electrode for obtaining the signal from the sensor device; and b) a transmitting electrode for transmitting the return signal.

In some particular embodiments, the receiving electrode of the emulator device is configured to communicate with a transmitting electrode on the sensor device, and the transmitting electrode of the emulator device is configured to communicate with a receiving electrode on the sensor device.

In other particular embodiments, the set of electrodes of the emulator device are in physical contact with the transmitting electrode and the receiving electrode on the sensor device during use, and the set of electrodes of the emulator device are electrically isolated from the transmitting electrode and the receiving electrode on the sensor device.

In still other particular embodiments, the set of electrodes of the emulator device are in physical contact with, and electrically connected with, the transmitting electrode and the receiving electrode on the sensor device during use.

In alternative particular embodiments, the set of electrodes of the emulator device are physically isolated from the transmitting electrode and the receiving electrode on the sensor device.

In other embodiments, the sensor device is in communication with the emulator device.

In various embodiments, the emulating includes replicating a complex impedance response of a benchmark electromagnetic measurement instrument to a test material at the obtained frequency.

In some cases, the emulating includes characterizing the obtained signal from the sensor device in terms of at least one of frequency and strength to determine a characteristic of the obtained signal.

In other cases, the emulating includes generating and transmitting a return signal that emulates the impedance response and is detectable by the sensor device, wherein the return signal is obtainable to standardize an impedance response of the sensor device based upon a benchmark sensor device.

Further, in other embodiments, the emulating includes: generating a return signal that emulates the impedance response and is detectable by the sensor device, wherein the return signal is comparable with a format of a predicted material configured to aid in calibrating the sensor device.

In various embodiments, the return signal includes data about a characteristic of the material.

In some cases, the obtained frequency includes a range of frequencies; and in other cases, the obtained frequency includes a single frequency.

Various additional embodiments include a computer program product having program code stored on a computer readable storage medium, which when executed by the at least one computing device, causes the at least one computing device to emulate an impedance response of a material by performing actions including: a) emulating an impedance response of a user-selected material based upon a type of the user-selected material and a sensor signal from a sensor device at a test frequency.

In various embodiments, the program code further causes the at least one computing device to evaluate characteristics of the sensor signal.

In some embodiments, the emulating further includes generating a return signal detectable by the sensor device, the return signal including the emulated impedance response at the test frequency of the sensor signal.

In other embodiments, the program code further provides instructions for an electronic circuit to generate the return signal.

In various other embodiments, the return signal includes data about a characteristic of the material.

In some embodiments, the program code further causes the at least one computing device to obtain a complex impedance response of a benchmark sensor device prior to the emulating.

When used herein, the term "transmit", when used with communication between computing means or other devices, is defined to mean transmission by wire, wireless (including Bluetooth or wireless phone networks), networks, or any other communication means which may be currently available or become available to one skilled in the art.

Data storage includes various storage types including printed, analog, or digital means. These recording means may be local such as paper, tape, disks, solid state memory. The data storage may be part of a local network, wide area network, the cloud, or any other data storage means which may become available to one skilled in the art.

It is understood that time and location logging may be incorporated into any measurement device shown and/or described herein by using GPS or other means.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It is further understood that the terms "front" and "back" are not intended to be limiting and are intended to be interchangeable where appropriate.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. An electromagnetic emulator system for emulating an impedance response of a calibration material, the system comprising:
    an emulator device including:
        an emulator circuit;
        a set of electrodes coupled with the emulator circuit, the set of electrodes including: a receiving electrode, and a transmitting electrode; and
    at least one computing device coupled with the emulator device and programmed to perform actions including:
        receiving instructions indicating a type of the calibration material to be emulated;
        receiving, via the receiving electrode, a signal from a sensor device at a received frequency, the received frequency being one of a single frequency or a frequency range, wherein the receiving electrode of the emulator device is configured to communicate with a transmitting electrode on the sensor device; and
        emulating the impedance response of the calibration material at the received frequency in response to determining the type of the calibration material, a type of the sensor device and the received frequency of the signal from the sensor device, wherein the emulating includes:
            generating a return signal that emulates the impedance response of the calibration material and is detectable by the sensor device; and
            transmitting the return signal at the transmitting electrode of using the emulator device, the transmitting electrode of the emulator device configured to communicate with a receiving electrode on the sensor device,
        wherein the emulating includes synchronizing a frequency of the return signal with the received frequency of the signal from the sensor device, wherein the emulator circuit generates the return signal, the return signal having a difference in amplitude and phase from the signal received from the sensor device, the difference in amplitude and phase corresponding with an expected change in the signal received from the sensor device after traveling through the calibration material.

2. The system of claim 1, wherein the set of electrodes on the emulator device are in physical contact with the transmitting electrode and the receiving electrode on the sensor device, and the set of electrodes on the emulator device are electrically isolated from the transmitting electrode and the receiving electrode on the sensor device.

3. The system of claim 1, wherein the set of electrodes on the emulator device are in physical contact with, and electrically connected with, the transmitting electrode and the receiving electrode on the sensor device.

4. The system of claim 1, wherein the set of electrodes on the emulator device are physically isolated from the transmitting electrode and the receiving electrode on the sensor device.

5. The system of claim 1, wherein the emulating includes replicating the complex impedance response of a benchmark electromagnetic measurement instrument to the calibration material at the obtained frequency.

6. The system of claim 1, wherein the emulating includes characterizing the obtained signal from the sensor device in terms of at least one of signal frequency or signal strength to determine a characteristic of the obtained signal.

7. The system of claim 1, wherein the return signal is configured to standardize an impedance response of the sensor device based upon a benchmark sensor device.

8. The system of claim 1, wherein the emulating includes:
    wherein the return signal is comparable with a format of a predicted material configured to aid in calibrating the sensor device.

9. The system of claim 1, wherein the emulating further includes selecting an equivalent circuit type for the emulator circuit to emulate the impedance response of the calibration material based upon the frequency of the received signal from the sensor device.

10. The system of claim 9, wherein the expected change in the signal is determined using an impedance map correlating the type of the calibration material and the type of the sensor device over a range of frequencies.

11. The system of claim 1, wherein the at least one computing device is configured to determine the frequency of the received signal from the sensor device without programmed or inputted information about the signal from the sensor device.

12. The system of claim 1, wherein the at least one computing device emulates the impedance response of the calibration material at the obtained frequency without prior information about the signal from the sensor device.

13. The system of claim 12, wherein emulating the impedance response of the calibration material at the frequency of the received signal is performed with only the type of the calibration material as inputted to the at least one computing device, the type of the sensor device as inputted to the at least one computing device and the frequency of the received signal from the sensor device as received at the receiving electrode.

14. A method of standardizing a sensor device for measuring a characteristic of a calibration material, the method comprising:
    obtaining benchmark impedance response data for the calibration material;
    positioning the sensor device in communication with an emulator system, the emulator system including:
        an emulator device including an emulator circuit; and a set of electrodes coupled with the emulator circuit, the set of electrodes including: a receiving electrode, and a transmitting electrode; and at least one computing device coupled with the emulator device;
selecting a type of the calibration material;
initiating a sensing signal to the receiving electrode of the emulator device from the sensor device at a sensing frequency, the sensing frequency being one of a single frequency or a frequency range;
receiving a return signal from the transmitting electrode of the emulator system, the return signal emulating an impedance response of the calibration material and being detectable by the sensor device, wherein the return signal is generated in response to determining the type of the calibration material, a type of the sensor device and the sensing signal from the sensor device, wherein the emulating includes synchronizing a frequency of the return signal with the frequency of the received signal from the sensor device; and
calibrating the sensor device using the return signal and the benchmark impedance response data.

15. The method of claim 14, wherein the calibrating includes applying a correlation method to match the return signal with the benchmark impedance response data at the sensing frequency.

16. The method of claim 14, wherein the emulator system receives the sensor signal and characterizes the sensor signal in terms of frequency and strength to determine characteristics of the return signal.

17. The method of claim 14, wherein the at least one computing device is configured to communicate with the sensor device and the emulator device and provide operating instructions to at least one of the sensor device or the emulator device.

18. The method of claim 14, wherein the at least one computing device is at least partially contained in one of the sensor device or the emulator system.

19. The method of claim 14, wherein the set of electrodes on the emulator device are in physical contact with the transmitting electrode and the receiving electrode on the sensor device, and the set of electrodes on the emulator device are electrically isolated from the transmitting electrode and the receiving electrode on the sensor device.

20. The method of claim 14, wherein the set of electrodes on the emulator device are in physical contact with, and electrically connected with, the transmitting electrode and the receiving electrode on the sensor device.

21. The method of claim 14, wherein the set of electrodes on the emulator device are physically isolated from the transmitting electrode and the receiving electrode on the sensor device.

22. The method of claim 14, wherein the emulating further includes selecting an equivalent circuit type for the emulator circuit to emulate the impedance response of the calibration material based upon the sensing frequency of the sensing signal, wherein the emulator circuit generates the return signal, the return signal having a difference in amplitude and phase from the sensing signal, the difference in amplitude and phase corresponding with an expected change in the sensing signal after traveling through the calibration material.

23. The method of claim 22, wherein the expected change in the sensing signal is determined using an impedance map correlating the type of the calibration material and the type of the sensor device over a range of frequencies.

24. An electromagnetic emulator system for emulating an impedance response of a user-selected type of calibration material, the system comprising:

an emulator device including an emulator circuit, and a set of electrodes coupled with the emulator circuit, the set of electrodes including: a receiving electrode, and a transmitting electrode; and
at least one computing device coupled with the emulator device and programmed to perform actions including emulating the impedance response of the user-selected calibration material at a received frequency in response to determining the type of the user-selected calibration material and a frequency of a received signal from a sensor device,
wherein the emulating includes generating a return signal that emulates the impedance response of the user-selected type of calibration material and is detectable by the sensor device, wherein the emulating includes synchronizing a frequency of the return signal with the frequency of the received signal from the sensor device, wherein the emulator circuit generates the return signal, the return signal having a difference in amplitude and phase from the signal received from the sensor device, the difference in amplitude and phase corresponding with an expected change in the signal received from the sensor device after traveling through the user-selected type of the calibration material.

25. The system of claim 24, wherein the receiving electrode of the emulator device is configured to communicate with a transmitting electrode on the sensor device, and the transmitting electrode of the emulator device is configured to communicate with a receiving electrode on the sensor device.

26. The system of claim 25, wherein the set of electrodes of the emulator device are in physical contact with the transmitting electrode and the receiving electrode on the sensor device during use, and the set of electrodes of the emulator device are electrically isolated from the transmitting electrode and the receiving electrode on the sensor device.

27. The system of claim 25, wherein the set of electrodes of the emulator device are in physical contact with, and electrically connected with, the transmitting electrode and the receiving electrode on the sensor device during use.

28. The system of claim 25, wherein the set of electrodes of the emulator device are physically isolated from the transmitting electrode and the receiving electrode on the sensor device.

29. The system of claim 24, wherein the emulating includes replicating a complex impedance response of a benchmark electromagnetic measurement instrument to a test material at the frequency of the received signal.

30. The system of claim 24, wherein the emulating includes characterizing the received signal from the sensor device in terms of at least one of frequency and strength to determine a characteristic of the received signal.

31. The system of claim 24, wherein the return signal is obtainable to standardize an impedance response of the sensor device based upon a benchmark sensor device.

32. The system of claim 24, wherein the frequency of the received signal includes a range of frequencies.

33. The system of claim 24, wherein the frequency of the received signal includes a single frequency.

34. The system of claim 24, wherein the emulating further includes selecting an equivalent circuit type for the emulator circuit to emulate the impedance response of the calibration material based upon the frequency of the received signal from the sensor device, wherein the emulator circuit generates the return signal, the return signal having a difference in amplitude and phase from the signal from the sensor device, the difference in amplitude and phase corresponding with an expected change in the signal from the sensor device after traveling through the calibration material.

35. The system of claim 34, wherein the expected change in the signal is determined using an impedance map correlating the type of the calibration material and the type of the sensor device over a range of frequencies.

36. A computer program product comprising program code stored on a non-transitory computer readable storage medium, which when executed by the at least one computing device, causes the at least one computing device to emulate an impedance response of a calibration material by performing actions including:

emulating an impedance response of a user-selected calibration material in response to determining a type of the user-selected calibration material and a test frequency of a received sensor signal from a sensor device, wherein the emulating further includes selecting an equivalent circuit type for an emulator circuit coupled with the at least one computing device to emulate the impedance response of the calibration material in response to determining the test frequency of the sensor signal; and instructing the emulator circuit coupled with the at least one computing device to generate a return signal, wherein the return signal is detectable by the sensor device, the return signal including the emulated impedance response at the test frequency of the sensor signal, wherein the return signal has a difference in amplitude and phase from the sensor signal, the difference in amplitude and phase corresponding with an expected change in the sensor signal after traveling through the calibration material.

37. The computer program product of claim 36, wherein the program code further causes the at least one computing device to obtain a complex impedance response of a benchmark sensor device prior to the emulating.

38. The computer program product of claim 37, wherein the expected change in the signal is determined using an impedance map correlating the type of the calibration material and the type of the sensor device over a range of frequencies.

* * * * *